United States Patent
Geva et al.

(10) Patent No.: US 12,102,627 B2
(45) Date of Patent: Oct. 1, 2024

(54) USE OF PRIDOPIDINE FOR TREATING RETT SYNDROME

(71) Applicant: PRILENIA NEUROTHERAPEUTICS LTD., Herzliya (IL)

(72) Inventors: Michal Geva, Even-Yehuda (IL); Ralph Laufer, Tel Aviv (IL); Michael Hayden, Herzliya (IL)

(73) Assignee: Prilenia Neurotherapeutics Ltd., Yakum (IL)

( * ) Notice: Subject to any disclaimer, the term of this patent is extended or adjusted under 35 U.S.C. 154(b) by 741 days.

(21) Appl. No.: 16/952,123

(22) Filed: Nov. 19, 2020

(65) Prior Publication Data

US 2021/0106572 A1 Apr. 15, 2021
US 2023/0165849 A2 Jun. 1, 2023

Related U.S. Application Data

(63) Continuation-in-part of application No. 16/332,369, filed as application No. PCT/US2017/051803 on Sep. 15, 2017.

(60) Provisional application No. 62/395,854, filed on Sep. 16, 2016.

(51) Int. Cl.
 A61K 31/451 (2006.01)
 A61K 9/00 (2006.01)
 A61P 25/14 (2006.01)

(52) U.S. Cl.
 CPC .......... A61K 31/451 (2013.01); A61K 9/0019 (2013.01); A61K 9/0053 (2013.01); A61P 25/14 (2018.01)

(58) Field of Classification Search
 CPC .............................. A61K 31/451; A61P 25/14
 See application file for complete search history.

(56) References Cited

U.S. PATENT DOCUMENTS

| | | |
|---|---|---|
| 6,903,120 B2 | 6/2005 | Sonesson et al. |
| 7,923,459 B2 | 12/2011 | Gauthier et al. |
| 9,006,445 B2 | 4/2015 | Sonesson et al. |
| 9,012,476 B2 | 4/2015 | Zimmermann et al. |
| 9,139,525 B2 | 9/2015 | Wikström |
| RE46,117 E | 8/2016 | Sonesson et al. |
| 9,796,673 B2 | 10/2017 | Wu et al. |
| 9,814,706 B2 | 11/2017 | Zimmermann et al. |
| 10,047,049 B2 | 8/2018 | Barel et al. |
| 10,130,621 B2 | 11/2018 | Schmidt et al. |
| 10,322,119 B2 | 6/2019 | Bassan et al. |
| 10,406,145 B2 | 10/2019 | Schmidt et al. |
| 2006/0135531 A1 | 6/2006 | Sonesson et al. |
| 2013/0197031 A1 | 1/2013 | Sonesson |
| 2013/0267552 A1 | 10/2013 | Waters et al. |
| 2015/0202302 A1 | 7/2015 | Licht et al. |
| 2016/0166559 A1 | 6/2016 | Sonesson |
| 2016/0095847 A1 | 7/2016 | Sonesson |
| 2016/0243098 A1 | 8/2016 | Geva et al. |
| 2017/0020854 A1 | 1/2017 | Licht et al. |
| 2017/0266170 A1 | 9/2017 | Waters et al. |
| 2018/0055832 A1 | 3/2018 | Hayden et al. |
| 2018/0235950 A1 | 8/2018 | Sonesson |
| 2019/0015401 A1 | 1/2019 | Sonesson |
| 2019/0046516 A1 | 2/2019 | Russ et al. |
| 2019/0192496 A1 | 6/2019 | Hayden et al. |
| 2019/0231768 A1 | 8/2019 | Geva et al. |
| 2019/0209542 A1 | 11/2019 | Licht et al. |
| 2019/0336488 A1 | 11/2019 | Hayden et al. |
| 2019/0350914 A1 | 11/2019 | Geva et al. |
| 2019/0350915 A1 | 11/2019 | Bassan et al. |
| 2020/0030308 A1 | 1/2020 | Schmidt et al. |
| 2022/0023280 A1* | 1/2022 | Schmidt ............... A61K 31/451 |

FOREIGN PATENT DOCUMENTS

| | | | |
|---|---|---|---|
| CA | 2937243 A1 * | 7/2015 | ........... A61K 31/451 |
| WO | WO 2001/046145 | 6/2001 | |
| WO | WO 2005/121092 | 12/2005 | |
| WO | WO 2006/040155 | 4/2006 | |
| WO | WO 2018/053287 | 3/2008 | |
| WO | WO 2008/127188 | 10/2008 | |
| WO | WO 2012/002863 | 5/2012 | |
| WO | WO 2013/034622 | 3/2013 | |
| WO | WO 2013/086425 | 6/2013 | |
| WO | WO 2013/152105 | 10/2013 | |
| WO | WO 2014/205229 | 12/2014 | |
| WO | WO 2015/112601 | 7/2015 | |
| WO | WO 2016/138130 | 1/2016 | |
| WO | WO 2016/138135 | 1/2016 | |
| WO | WO 2016/003919 | 7/2016 | |
| WO | WO 2017/015609 | 1/2017 | |
| WO | WO 2017/015615 | 1/2017 | |
| WO | WO 2017/147366 | 8/2017 | |

(Continued)

OTHER PUBLICATIONS

Sun et al., "The Ups and Downs of BDNF in Rett Syndrome", Neuron, vol. 49, No. 3, pp. 321-329 (2006).*
Amaral et al. "TRPC channels as novel effectors of BDNF signaling: Potential implications for Rett syndrome" Pharmacology & therapeutics. Feb. 2007;113(2):394.
CSID:25948790, www.chemspider.com/Chemical-Structure.25948790. html (accessed 23:27, Jul. 15, 2016).
CSID:7971505, www.chemspider.com/Chemical-Structure.7971505. html (accessed 23:33, Jul. 15, 2016).

(Continued)

*Primary Examiner* — Kevin E Weddington

(74) *Attorney, Agent, or Firm* — Mark S. Cohen; PEARL COHEN ZEDEK LATZER BARATZ LLP

(57) ABSTRACT

The subject invention provides a method for treating a subject afflicted with Rett syndrome comprising administering to the subject an effective amount of pridopidine so as to thereby treat the subject.

25 Claims, 13 Drawing Sheets

Specification includes a Sequence Listing.

(56) References Cited

FOREIGN PATENT DOCUMENTS

| WO | WO 2018/039475 | 1/2018 |
| WO | WO 2018/039477 | 1/2018 |
| WO | WO 2018/053275 | 3/2018 |
| WO | WO 2018/053280 | 3/2018 |
| WO | WO 2018/136600 | 7/2018 |
| WO | WO 2019/036358 | 2/2019 |
| WO | WO 2019/050775 | 3/2019 |
| WO | WO 2019/046568 | 7/2019 |
| WO | WO 2020/188558 | 9/2020 |

OTHER PUBLICATIONS

De Yebenes et al. "Pridopidine for the treatment of motor function in patients with Huntington's disease (MermaIHD): a phase 3, randomised, double-blind, placebo-controlled trial" The Lancet Neurology. Dec. 1, 2011;10(12):1049-57.

Geva et al. "Pridopidine activates neuroprotective pathways impaired in Huntington Disease" Human molecular genetics. Sep. 15, 2016;25(18):3975-87.

Geva et al. "Pridopidine Treatment Recovers Gait Abnormalities and Rescues Impaired BDNF Expression in a Rett Syndrome Mouse Model" 2018 (P3. 324).

Guy et al. "A mouse Mecp2-null mutation causes neurological symptoms that mimic Rett syndrome" Nature genetics. Mar. 2001;27(3):322-6.

Huntington Study Group HART Investigators "A randomized, double-blind, placebo-controlled trial of pridopidine in Huntington's disease" Movement Disorders. Sep. 2013;28(10):1407-15.

International Search Report for PCT Application No. PCT/US2017/051803 dated Dec. 22, 2017.

Isaias et al. "Gait initiation in children with Rett syndrome" PloS One. 2014;9(4).

Ponten et al "In vivo pharmacology of the dopaminergic stabilizer pridopidine" European journal of pharmacology. Oct. 10, 2010;644(1-3):88-95.

Pozzo-Miller et al. "Rett syndrome: reaching for clinical trials" Neurotherapeutics. Jul. 1, 2015;12(3):631-40.

Rabinovich-Guilatt et al. "The effect of mild and moderate renal impairment on the pharmacokinetics of pridopidine, a new drug for Huntington's disease" British journal of clinical pharmacology. Feb. 2016;81(2):246-55.

Ryskamp et al. "The sigma-1 receptor mediates the beneficial effects of pridopidine in a mouse model of Huntington disease" Neurobiology of disease. Jan. 1, 2017; 97:46-59.

Supplementary European Search Report for European Application No. 17851614.2 dated Apr. 30, 2020.

Weng et al. "Rett syndrome: from bed to bench" Pediatrics & Neonatology. Dec. 1, 2011;52(6):309-16.

Djukic, A., et al. (2016). Pharmacologic treatment of Rett syndrome with glatiramer acetate. Pediatric neurology, 61, 51-57.

Li, W. et al. (2014). BDNF deregulation in Rett syndrome. *Neuropharmacology*, 76, 737-746.

Van Der Krogt, M. M., et al. (2012). How robust is human gait to muscle weakness ?. *Gait & posture*, 36(1), 113-119.

Castillo-Mariqueo, L., et al. (2021). Modeling functional limitations, gait impairments, and muscle pathology in alzheimer's disease: Studies in the 3xtg-ad mice. Biomedicines, 9(10), 1365.

Khwaja, O. S., et al. (2014). Safety, pharmacokinetics, and preliminary assessment of efficacy of mecasermin (recombinant human IGF-1) for the treatment of Rett syndrome. Proceedings of the National Academy of Sciences, 111(12), 4596-4601.

Mao, Y., et al. (2021). Anti-Semaphorin 4D rescues motor, cognitive, and respiratory phenotypes in a Rett syndrome mouse model. International Journal of Molecular Sciences, 22(17), 9465.

Van Der Krogt, M. M., et al. (2012). How robust is human gait to muscle weakness ?. Gait & posture, 36(1), 113-119.

Yahia, A., et al. (2011). Relationship between muscular strength, gait and postural parameters in multiple sclerosis. Annals of physical and rehabilitation medicine, 54(3), 144-155.

* cited by examiner

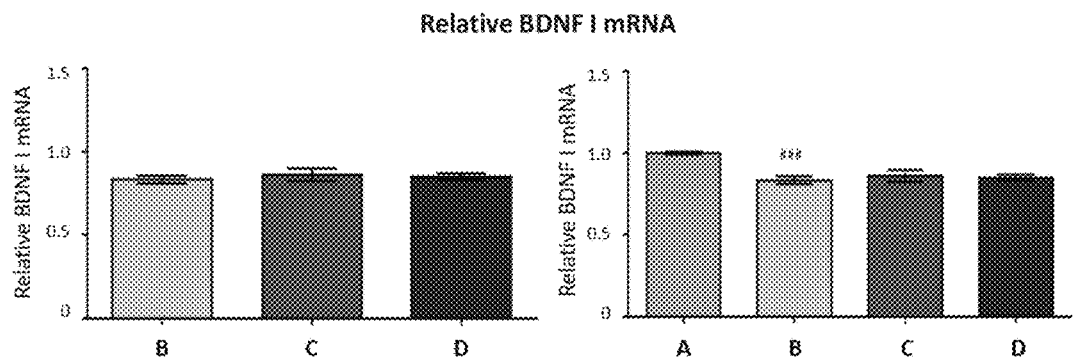
FIGURE 7A
FIGURE 7B
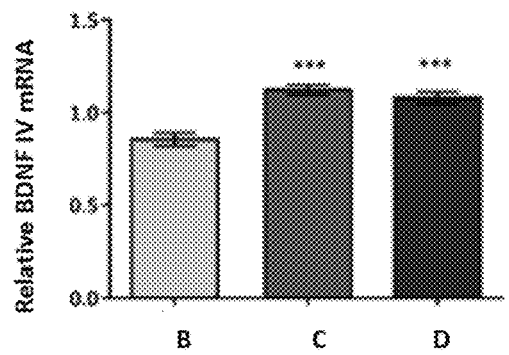
FIGURE 8A
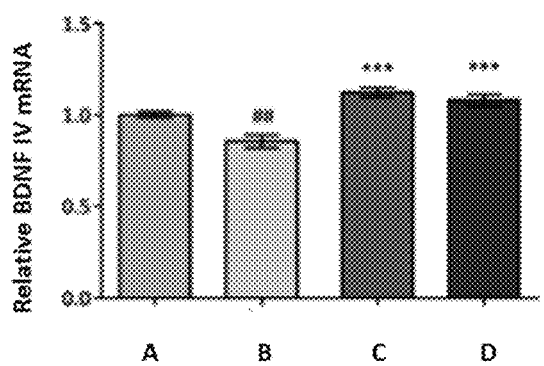
FIGURE 8B

USE OF PRIDOPIDINE FOR TREATING RETT SYNDROME

CROSS REFERENCE TO RELATED APPLICATIONS

This application is Continuation-in-Part Application from U.S. application Ser. No. 16/332,369 filed Mar. 12, 2019; which is a National Phase Application of PCT International Application No. PCT/US2017/051803, International Filing Date Sep. 15, 2017, claiming the benefit of U.S. Patent Application No. 62/395,854, filed Sep. 16, 2016, the contents of which are hereby incorporated by reference in their entirety.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

SEQUENCE LISTING STATEMENT

The ASCII file, entitled P-584310-US1-SQL-15SEP17.txt, created on Sep. 15, 2017, comprising 3,067 bytes, submitted concurrently with the filing of this application is incorporated herein by reference.

BACKGROUND

Rett Syndrome

Rett syndrome (RTT) is a neurological disorder estimated to affect 1 in every 10,000 to 15,000 live female births in all racial and ethnic groups. (Amaral 2007).

In 95%-97% of cases, RTT is caused by a mutation in the Methyl-CpG binding Protein 2 (MeCP2) gene located on the X chromosome. (Isaias 2014). The mutation is usually random and spontaneous. In less than 1% of recorded cases, the mutation is inherited or passed from one generation to the next. The MeCP2 gene is involved in the production of the methyl-cystine binding protein 2 (MeCP2) protein. The MeCP2 protein binds methylcytosine and 5-hydroxymethycytosine at CpG sites in promoter regions of target genes, controlling their transcription by recruiting co-repressors and co-activators. (Pozzo-Miller 2015). RTT, in rare cases, may also be caused by partial gene deletions or mutations in other genes such as cyclin-dependent kinase-like 5 (CDKL5), Forkhead box protein G1 (FOXG1), and possibly other genes that have not yet been identified.

RTT manifests with incoordination, intellectual decline, gait abnormalities, and seizures. (Weng 2011). Currently, there is no treatment for RTT.

Pridopidine

Pridopidine (4-[3-(methylsulfonyl)phenyl]-1-propyl-piperidine) (formerly known as ACR16) is a drug under development for treatment of Huntington disease. The chemical name of pridopidine is 4-(3-(Methylsulfonyl)phenyl)-1-propylpiperidine and its Chemical Registry Number is CAS 346688-38-8 (CSID:7971505 2016). The Chemical Registry number of pridopidine hydrochloride is 882737-42-0 (CSID:25948790 2016).

Pridopidine has a selective and high affinity for the sigma-1 receptor (SIR, binding IC50~100 nM), with low-affinity binding to additional receptors, including the dopamine D2/D3 receptors (in the micromolar range).

The Si R is an endoplasmic reticulum (ER) chaperone protein implicated in cellular differentiation, neuroplasticity, neuroprotection and cognitive function in the brain. Activation of the SIR by pridopidine leads to upregulation of pathways known to promote neuronal plasticity and survival, including the AKT/Phosphoinositide kinase (PI3K) pathway and the dopamine receptor 1 (D1R). Pridopidine upregulates the secretion and downstream signaling of the neuroprotective brain-derived neuroptrophic factor (BDNF) (Geva et al., 2016).

A decrease in BDNF is associated with Rett pathogenesis. Homeostatic synaptic plasticity (HSP), the processes that maintain the stability of neuronal networks and underlie learning and cognitive capabilities, are regulated by BDNF (Smith-Dijak et al., 2019). HSP is also disrupted in Rett syndrome. Mecp2-deficient neurons show impaired homeostatic synaptic plasticity (Xin xu and Pozzo-Miller, J physiolo 2017). Pridopidine restores impaired HSP in cultured cortical neurons from the HD YAC128 mouse model (Smith-Dijak et al., 2019).

Modulation of the BDNF pathway is a major component of pridopidine's SIR-mediate neuroprotective effects.

SUMMARY OF THE INVENTION

This invention provides a method for treating a subject afflicted with Rett syndrome (RTT) comprising administering to the subject an effective amount of pridopidine so as to thereby treat the subject.

This invention also provides a pharmaceutical composition comprising an amount of pridopidine for use in treating a subject afflicted with RTU.

This invention also provides a pharmaceutical composition in unit dosage form, useful in treating a subject afflicted with RTT.

This invention also provides a use of an amount of pridopidine in the manufacture of a medicament for treating a subject afflicted with RTT.

This invention also provides a use of an amount of pridopidine for treating a subject afflicted with RTT.

This invention also provides a method for increasing brain-derived neurotrophic factor (BDNF) level in a subject afflicted with RTT comprising administering to the subject an effective amount of pridopidine so as to thereby increase BDNF serum level in the subject.

DESCRIPTION OF THE FIGURES

In FIGS. 6A-6C, 7A-7B, 8A-8B, 9A-9B, 10A-10B. These figures display mRNA levels of BDNF transcripts measured in the brains of female heterozygous MeCP2 (Rett) mice. Column A represents vehicle treated WT mice, column B represents vehicle treated Rett female mice, column C represents pridopidine treated Rett female mice (3 mg/kg) and column D represents pridopidine treated Rett female mice (30 mg/kg).

FIGS. 6A-6C: Relative mRNA expression of whole brain control housekeeping genes: ATP5B (6A), GAPDH (6B) and RPL13A (6C); each normalized to the geometric means of the other two genes. Pridopidine did not affect the expression of control housekeeping genes.

FIGS. 7A-7B: Relative mRNA expression of BDNF I in whole brain: Drug efficacy in Rett female mice (7A), Extent of BDNF I transcript rescue as compared to WT, vehicle treated group (7B). Pridopidine had no effect on the mRNA levels of BDNF I.

FIGS. 8A-8B: Relative mRNA expression of BDNF IV in whole brain: Drug efficacy in Rett female mice (8A), Extent of BDNF IV transcript rescue as compared to WT, vehicle treated group (8B). Pridopidine significantly increased the mRNA levels of BDNF IV.

FIGS. 9A-9B: Relative mRNA expression of BDNF VI in whole brain: Drug efficacy in Rett female mice (9A), Extent of BDNF VI transcript rescue as compared to WT, vehicle treated group (9B). Pridopidine had no effect on the mRNA levels of BDNF VI.

FIGS. 10A-10B: Relative mRNA expression of BDNF IX (full length) in whole brain: Drug efficacy in Rett female mouse model (10A), Extent of BDNF IX transcript rescue as compared to WT, vehicle treated group (10B). Pridopidine significantly increased the mRNA levels of BDNF IX.

At week 26, pridopidine 45 mg bid improves gait function vs placebo (Δ from placebo −0.48, p=0.0563). Table 1, below, accompanies the figure. At week 52 Pridopidine 45 mg bid treatment shows a trend towards improvement compared to placebo (Δ from placebo −0.41, negative values indicate an improvement).

TABLE 1

Pridopidine 45 mg bid improves gait and balance in early HD patients (HD1 + HD2, TFC 7-13) at 26 and 52 weeks in PRIDE-HD

|  | Placebo | Pridopidine 45 mg bid |
| --- | --- | --- |
| Week 26 | | |
| N | 62 | 59 |
| from baseline (SE)Δ | 0.14 (0.17) | −0.34 (0.18) |
| from placeboΔ |  | −0.48 |
| p-value |  | 0.0563 |
| Week 52 | | |
| N | 62 | 59 |
| Δ from baseline (SE) | 0.52 (0.21) | 0.11 (0.22) |

TABLE 1-continued

Pridopidine 45 mg bid improves gait and balance in early HD patients (HD1 + HD2, TFC 7-13) at 26 and 52 weeks in PRIDE-HD

| | Placebo | Pridopidine 45 mg bid |
|---|---|---|
| Δ from placebo | | −0.41 |
| p-value | | 0.18 |

Figure 14A:
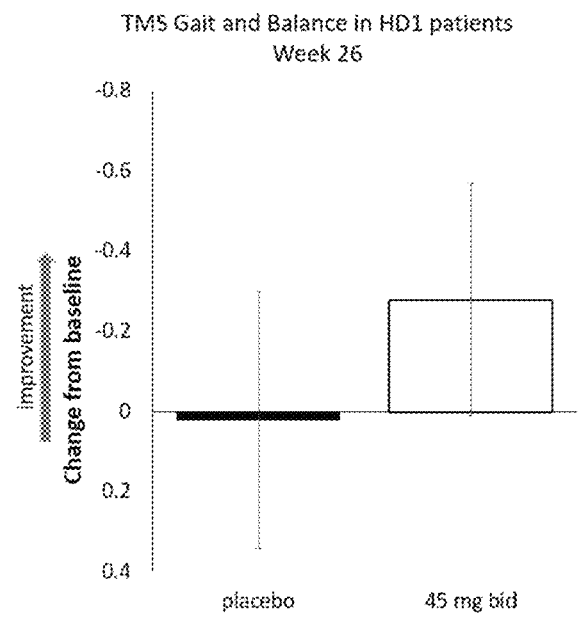
Figure 14B:
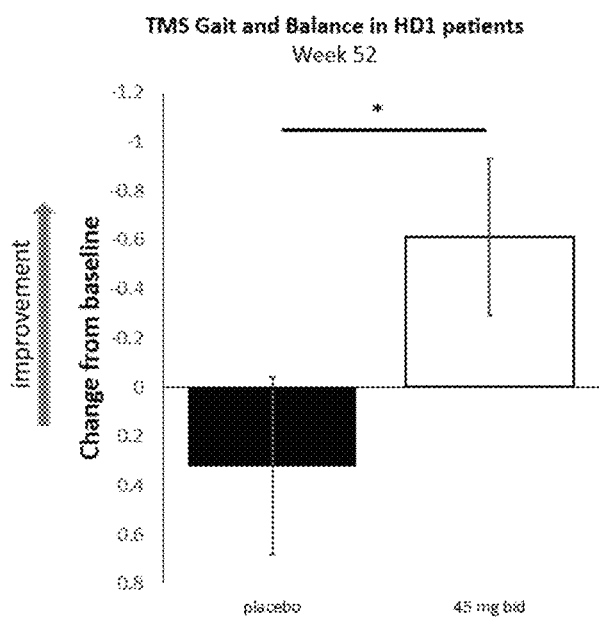

FIG. 14A-14B: Change from baseline in UHDRS TMS gait balances at week 26 (A) and at week 52 (B) in HD1 (baseline TFC 11-13) patients in the PRIDE-HD study. Pridopidine efficacy was assessed throughout the 52-week period using Mixed Models Repeated Measures (MMRM) analyses of change from baseline in the Unified Huntington's Disease Rating Scale Total Motor Score gait and balance (UHDRS TMS; gait and balance).

At week 26, pridopidine shows a trend towards improvement (Δ from placebo −0.31) Table 2, below, accompanies the figure. At week 52, Pridopidine 45 mg bid treatment shows a significant improvement compared to placebo (Δ from placebo −0.94, p=0.0445, negative values indicate an improvement).

TABLE 2

Pridopidine 45 mg bid improves gait and balance in HD1 (TFC 11-13) patients at 26 and 52 weeks in PRIDE-HD

| | Placebo | Pridopidine 45 mg bid |
|---|---|---|
| | Week 26 | |
| N | 12 | 17 |
| Δ from baseline (SE) | 0.02 (0.32) | −0.29 (0.28) |
| Δ from placebo | | −0.31 |
| p-value | | 0.4459 |
| | Week 52 | |
| N | P | 17 |
| Δ from baseline (SE) | 0.32 (0.36) | −0.61 (0.32) |
| Δ from placebo | | −0.94 |
| p-value | | 0.0445 |

Figure 15A:
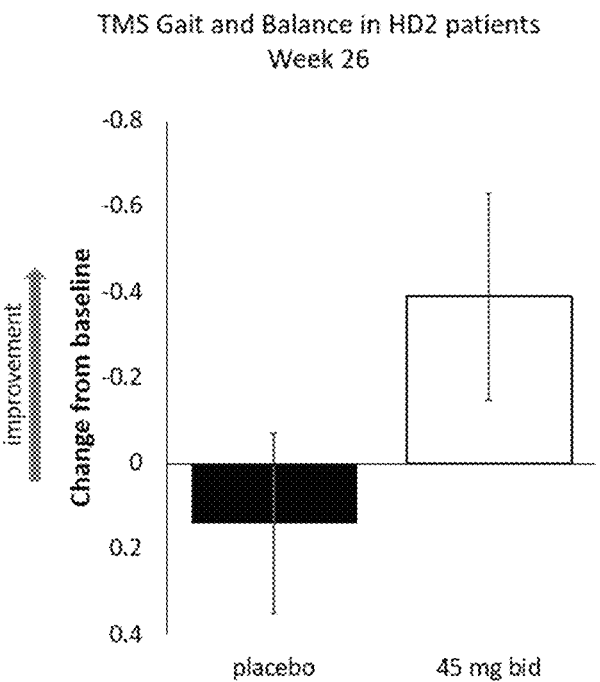
Figure 15B:
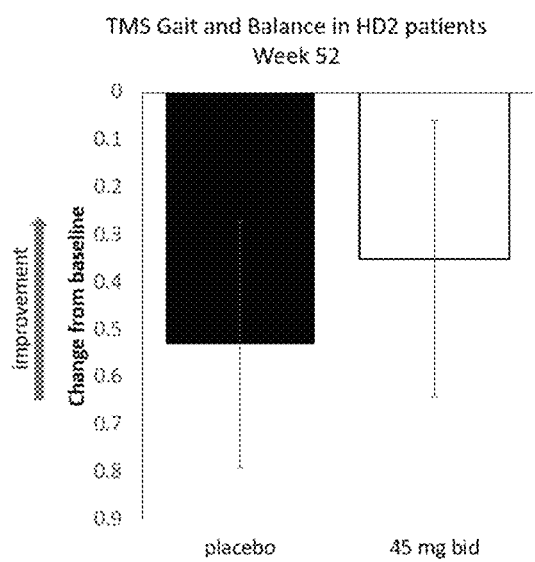

FIG. 15A-15B: Change from baseline in UHDRS TMS gait balances at week 26 (A) and week 52 (B) in HD2 (baseline TFC 7-10) patients in the PRIDE-HD study. Pridopidine efficacy was assessed throughout the 52-week period using Mixed Models Repeated Measures (MMRM) analyses of change from baseline in the Unified Huntington's Disease Rating Scale Total Motor Score gait and balance (UHDRS TMS; gait and balance). At both 26 weeks and 52 weeks, pridopidine 45 mg bid treatment shows a trend towards improvement compared to placebo (Δ from placebo is −0.53 and −0.18 for weeks 26 and 52, respectively; negative values indicate an improvement). Table 3, below, accompanies the figure.

TABLE 3

Pridopidine 45 mg bid improves gait and balance in HD2 patients (TFC 7-10) at 26 and 52 weeks in PRIDE-HD

| | Placebo | Pridopidine 45 mg bid |
|---|---|---|
| | Week 26 | |
| N | 50 | 42 |
| Δ from baseline (SE) | 0.14 (0.21) | −0.39 (0.24) |
| Δ from placebo | | −0.53 |
| p-value | | 0.0936 |

TABLE 3-continued

Pridopidine 45 mg bid improves gait and balance in HD2 patients (TFC 7-10) at 26 and 52 weeks in PRIDE-HD

| | Placebo | Pridopidine 45 mg bid |
|---|---|---|
| | Week 52 | |
| N | 50 | 42 |
| Δ from baseline (SE) | 0.53 (0.26) | 0.35 (0.29) |
| Δ from placebo | | −0.18 |
| p-value | | 0.6352 |

DETAILED DESCRIPTION OF THE INVENTION

This invention provides a method for treating a subject afflicted with Rett syndrome (RTT) comprising administering to the subject an effective amount of pridopidine so as to thereby treat the subject.

In one embodiment, this invention provides a method for delaying the onset, preventing worsening, delaying worsening, or improving at least one of at least one symptom associated with Rett syndrome in a subject afflicted with Rett syndrome.

In one embodiment, the subject is a human patient. In one embodiment, the human patient is female. In another embodiment, the human patient is male.

In one embodiment, the subject has a mutation in the methyl CpG binding protein 2 (MECP2) gene. In one embodiment, the subject has a mutation in the cyclin-dependent kinase-like 5 (CDKL5) gene. In one embodiment, subject has a mutation in the Forkhead box protein G1 (FOXG1) gene.

In one embodiment, the pridopidine is pridopidine hydrochloride. In another embodiment, the pridopidine is hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, the naphthalene-2-sulphonate, phthalate, salicylate, sorbate, stearate, succinate, tartrate or toluene-p-sulphonate salt.

In one embodiment, the pridopidine is administered orally, nasally, inhaled, by subcutaneous injection, or through an intravenous, intraperitoneal, intramuscular, intranasal, buccal, vaginal, rectal, intraocular, intrathecal, topical or intradermal route. In one embodiment, the pridopidine is administered orally.

In one embodiment, the pridopidine is administered in the form of an aerosol, an inhalable powder, an injectable, a liquid, a gel, a solid, a capsule or a tablet.

In one embodiment, the pridopidine is administered periodically.

In one embodiment, the pridopidine is administered less often than once daily. In one embodiment, the pridopidine is administered daily. In one embodiment, the pridopidine is administered once daily. In another embodiment, the pridopidine is administered more often than once daily. In one embodiment, the pridopidine is administered twice daily.

In one embodiment, the amount of pridopidine administered 0.5 mg/day-315 mg/day. In one embodiment, the amount of pridopidine administered 0.5 mg/day-50 mg/day. In one embodiment, the amount of pridopidine administered 0.5 mg/day-20 mg/day. In one embodiment, the amount of pridopidine administered 0.5 mg/day-10 mg/day. In one embodiment, the amount of pridopidine administered is 10 mg/day-315 mg/day. In one embodiment, the amount of pridopidine administered is 90 mg/day-315 mg/day. In one embodiment, the amount of pridopidine administered is 90 mg/day-225 mg/day. In one embodiment, the amount of pridopidine administered is 180 mg/day-225 mg/day. In another embodiment, the amount of pridopidine administered is about 20 mg/day, 22.5 mg/day, about 45 mg/day, about 67.5 mg/day, about 90 mg/day, about 100 mg/day, about 112.5 mg/day, about 125 mg/day, about 135 mg/day, about 150 mg/day, about 180 mg/day, about 200 mg/day, about 225 mg/day, about 250 mg/day, or about 315 mg/day. In an embodiment, the amount of pridopidine administered is 45 mg/day. In an embodiment, the amount of pridopidine administered is 90 mg/day. In an embodiment, the amount of pridopidine administered is 180 mg/day. In an embodiment, the amount of pridopidine administered is 225 mg/day.

In one embodiment, the amount of pridopidine is administered in one dose per day. In one embodiment, the amount of pridopidine is administered in two doses per day.

In one embodiment, the amount of pridopidine administered in a dose is about 10 mg, about 22.5 mg, about 45 mg, about 67.5 mg, about 90 mg, about 100 mg, about 112.5 mg, about 125 mg, about 135 mg, about 150 mg, about 180 mg, about 200 mg, about 250 mg, or about 315 mg. In an embodiment, the amount of pridopidine administered in a dose is 45 mg. In an embodiment, the amount of pridopidine administered in a dose is 10-45 mg.

In one embodiment, the amount of pridopidine is administered in two doses per day at an amount of 45 mg per dose.

In one embodiment, the pridopidine is first administered from as from as early as 1 day after birth and older. In one embodiment, the pridopidine is first administered within 1 day after birth of the subject. In one embodiment, the pridopidine is first administered within 1 week after birth of the subject. In one embodiment, the pridopidine is first administered within 1 month after birth of the subject. In one embodiment, the pridopidine is first administered within 3 months after birth of the subject. In one embodiment, the pridopidine is first administered within 6 months afterbirth of the subject. In one embodiment, the pridopidine is first administered within 9 months after birth of the subject. In one embodiment, the pridopidine is first administered within 12 months after birth of the subject. In one embodiment, the pridopidine is first administered within 18 months after birth of the subject. In one embodiment, the pridopidine is first administered within 3 years after birth of the subject. In one embodiment, the pridopidine is first administered within 5 years afterbirth of the subject. In one embodiment, the pridopidine is first administered within 10 years after birth of the subject. In one embodiment, the pridopidine is first administered within 15 years after birth of the subject. In one embodiment, the pridopidine is first administered within 20 years after birth of the subject. In one embodiment, the pridopidine is first administered within 25 years afterbirth of the subject. In one embodiment, the pridopidine is first administered within 30 years after birth of the subject. In one embodiment, the pridopidine is first administered 30 years or more after birth of the subject.

In one embodiment, the periodic administration of pridopidine continues for at least 3 days, at least 30 days, at least 42 days, at least 8 weeks, at least 12 weeks, at least 24 weeks, at least 6 months, at least 1 year, at least 2 years, at least 5 years, at least 10 years, at least 15 years, at least 20 years, at least 25 years, or 30 years or more.

In one embodiment, the pridopidine treats the subject by delaying the onset of symptoms in the subject.

In one embodiment, pridopidine treats a subject afflicted with Rett syndrome by delaying the onset, preventing worsening, delaying worsening, or improving of at least one symptom in the subject. In one embodiment, pridopidine improves or delays the worsening of at least one symptom in the subject afflicted with Rett syndrome. In one embodiment, the pridopidine treats the subject by improving at least one symptom in the subject.

In one embodiment, the symptom is a delay in acquiring mobility skills. In one embodiment, the symptom is delayed sitting, crawling, and/or walking. In one embodiment, the symptom is a partial or complete loss of acquired mobility skills. In one embodiment, the symptom is decreased ability to sit, crawl, and/or walk. In one embodiment, the mobility skill is motor coordination skill.

In one embodiment, the symptom is abnormal gait. In one embodiment, the symptom is ataxia. In one embodiment, the symptom is apraxia. In one embodiment, the symptom is muscle weakness. In one embodiment, the symptom is spasticity. In one embodiment, the symptom is rigidity. In one embodiment, the symptom is impaired gait initiation.

In one embodiment, the symptom is abnormal muscle tone. In one embodiment, the symptom is hypotonia. In one embodiment, the symptom is peripheral vasomotor disturbance. In one embodiment, the symptom is scoliosis. In one embodiment, the symptom is impaired gait initiation.

In one embodiment, the symptom is a delay in acquiring purposeful hand skills. In one embodiment, the symptom is a partial or complete loss of acquired purposeful hand skills. In one embodiment, the symptom is abnormal hand movement. In one embodiment, the abnormal hand movement is wringing, squeezing, clapping, washing, tapping, rubbing, and/or repeatedly bringing hands to mouth.

In one embodiment, the symptom is a delay in acquiring communication skill. In one embodiment, the symptom is a partial or complete loss of acquired communication skill. In one embodiment, the communication skill is language skill. In one embodiment, the language skill is spoken language skill. In one embodiment, the communication skill is eye contact.

In one embodiment, the symptom is abnormal eye movement. In one embodiment, the abnormal eye movement is prolonged staring, excessive blinking, crossed eyes, and/or closing one eye at a time.

In one embodiment, the symptom is breathing irregularity. In one embodiment, the breathing irregularity occurs when the subject is awake. In one embodiment, the breathing irregularity is apnea. In one embodiment, the breathing irregularity is hyperventilation.

In one embodiment, the symptom is bruxism when the subject is awake.

In one embodiment, the symptom is increased irritability, decreased alertness, and/or decreased attention span. In one embodiment, the symptom is inappropriate laughing and/or screaming.

In one embodiment, the symptom is seizure.

In one embodiment, the symptom is cardiac abnormality. In one embodiment, the cardiac abnormality is bradycardia. In one embodiment, the cardiac abnormality is tachycardia.

In one embodiment, the symptom is decreased response to pain. In one embodiment, the symptom is growth retardation. In one embodiment, the symptom is microcephaly. In one embodiment, the symptom is impaired sleeping pattern. In one embodiment, the symptom is hypotrophic cold blue feet.

In one embodiment, the pridopidine improves the symptom by at least 5%. The pridopidine improves the symptom by at least 10%. In one embodiment, the pridopidine improves the symptom by at least 20%. In one embodiment, the pridopidine improves the symptom by at least 30%. In one embodiment, the pridopidine improves the symptom by at least 50%. In one embodiment, the pridopidine improves the symptom by at least 80%. In one embodiment, the pridopidine improves the symptom by 100%.

In one embodiment, the pridopidine treats the subject by improving the subject's ability to perform activities of daily living, perform domestic chores, manage finances, and/or perform an occupation. In one embodiment, the pridopidine treats the subject by reducing the level of nursing care needed by the subject.

In one embodiment, the pridopidine treats the subject by maintaining the subject's ability to perform activities of daily living, perform domestic chores, manage finances, and/or perform an occupation.

In one embodiment, the pridopidine is effective to increase the BDNF serum level in the subject. In one embodiment, the pridopidine is effective to increase the BDNF levels in the brain of the subject. In one embodiment, the pridopidine is effective to maintain the BDNF serum level in the subject.

This invention also provides a pharmaceutical composition comprising an amount of pridopidine for use in treating a subject afflicted with RTT.

This invention also provides a pharmaceutical composition in unit dosage form, useful in treating a subject afflicted with RTT.

In one embodiment, the amount of pridopidine administered 0.5 mg/day-315 mg/day. In one embodiment, the amount of pridopidine is 10 mg-315 mg. In one embodiment, the amount of pridopidine is 90 mg-315 mg. In one embodiment, the amount of pridopidine is 90 mg-225 mg. In another embodiment, the amount of pridopidine is about 22.5 mg, about 45 mg, about 67.5 mg, about 90 mg, about 100 mg, about 112.5 mg, about 125 mg, about 135 mg, about 150 mg, about 180 mg, about 200 mg, about 225 mg, about 250 mg, or about 315 mg. In an embodiment, the amount of pridopidine is 45 mg. In an embodiment, the amount of pridopidine is 90 mg. In an embodiment, the amount of pridopidine is 180 mg. In an embodiment, the amount of pridopidine is 225 mg.

This invention also provides a use of an amount of pridopidine in the manufacture of a medicament for treating a subject afflicted with RTT.

This invention also provides a use of an amount of pridopidine for treating a subject afflicted with RTT.

The invention also provides a package comprising:
  a) a pharmaceutical composition comprising an amount of pridopidine and a pharmaceutically acceptable carrier; and
  b) instructions for use of the pharmaceutical composition to treat a subject afflicted with RTT.

A therapeutic package for dispensing to, or for use in dispensing to, a subject afflicted with RTT, which comprises:
  a) one or more unit doses, each such unit dose comprising an amount of pridopidine effective to treat the subject afflicted with RTT, and
  b) a finished pharmaceutical container therefor, said container containing said unit dose or unit doses, said container further containing or comprising labeling directing the use of said package in treating the subject.

This invention also provides a method of increasing BDNF serum level in a subject afflicted with RTT comprising administering to the subject an effective amount of pridopidine so as to thereby increase BDNF serum level in the subject. This invention also provides a method of increasing BDNF brain level in a subject afflicted with RTT comprising administering to the subject an effective amount of pridopidine so as to thereby increase BDNF brain level in the subject.

For the foregoing embodiments, each embodiment disclosed herein is contemplated as being applicable to each of the other disclosed embodiments. In addition, the elements recited in method embodiments can be used in the pharmaceutical composition, use, and package embodiments described herein and vice versa.

Terms

As used herein, and unless stated otherwise, each of the following terms shall have the definition set forth below.

As used herein, "pridopidine" means pridopidine base or a pharmaceutically acceptable salt thereof, as well as derivatives or analogs thereof, for example deuterium-enriched pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference. "Deuterium-enriched" means that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%. Deuterium-enriched compounds may be obtained by exchanging hydrogen with deuterium or synthesizing the compound with deuterium-enriched starting materials.

Pridopidine Analogs

In some embodiments the methods of this invention make use of a pharmaceutical composition comprising pridopidine or pharmaceutically acceptable salt thereof and at least one analog thereof and pharmaceutically acceptable salt thereof. In another embodiment, the analog compounds of pridopidine or salts thereof are represented by the following structures of compounds 1-7:

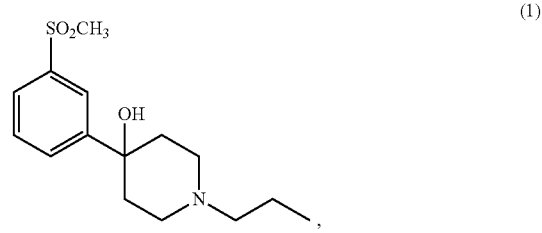
(1)

-continued

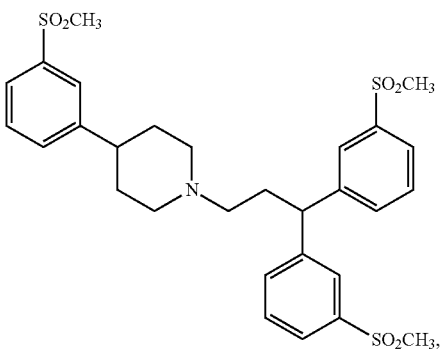
(2)

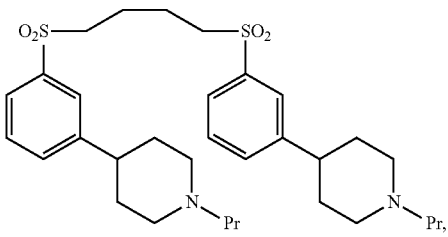
(3)

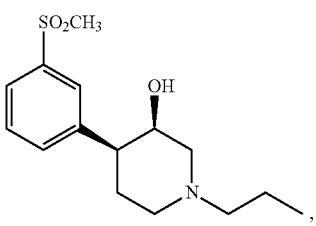
(4)

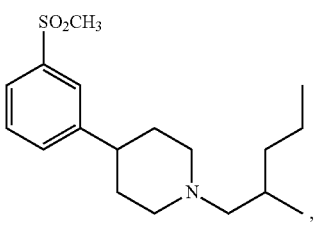
(5)

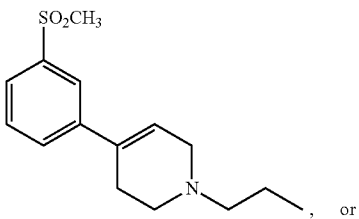
(6)

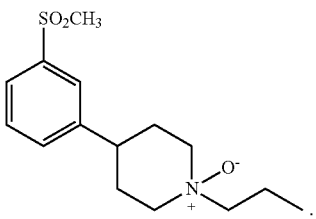
or
(7)

In other embodiments this invention provides a pharmaceutical composition comprising pridopidine or pharmaceutically acceptable salt thereof and compound 1 or pharmaceutically acceptable salt thereof. In other embodiments this invention provides a pharmaceutical composition comprising pridopidine or pharmaceutically acceptable salt thereof and compound 2 or pharmaceutically acceptable salt thereof. In other embodiments this invention provides a pharmaceutical composition comprising pridopidine or pharmaceutically acceptable salt thereof and compound 3 or pharmaceutically acceptable salt thereof. In other embodiments this invention provides a pharmaceutical composition comprising pridopidine or pharmaceutically acceptable salt thereof and compound 4 or pharmaceutically acceptable salt thereof. In other embodiments this invention provides a pharmaceutical composition comprising pridopidine or pharmaceutically acceptable salt thereof and compound 5 or pharmaceutically acceptable salt thereof. In other embodiments this invention provides a pharmaceutical composition comprising pridopidine or pharmaceutically acceptable salt thereof and compound 6 or pharmaceutically acceptable salt thereof. In other embodiments this invention provides a pharmaceutical composition comprising pridopidine or pharmaceutically acceptable salt thereof and compound 7 or pharmaceutically acceptable salt thereof. In other embodiments this invention provides a pharmaceutical composition comprising pridopidine or pharmaceutically acceptable salt thereof and compound 1 and compound 4 or pharmaceutically acceptable salt thereof. In other embodiments, the concentration of compounds 1, 2, 3, 4, 5, 6 or 7 or pharmaceutically acceptable salt thereof within the composition is between 0.001% w/w to 10% w/w. In other embodiments, the concentration of compounds 1, 2, 3, 4, 5, 6 or 7 or pharmaceutically acceptable salt thereof within the composition is between 0.001% w/w to 0.05% w/w. In other embodiments, the concentration of compounds 1, 2, 3, 4, 5, 6 or 7 or pharmaceutically acceptable salt thereof within the composition is between 0.001% w/w to 0.5% w/w. In other embodiments, the concentration of compounds 1, 2, 3, 4, 5, 6 or 7 or pharmaceutically acceptable salt thereof within the composition is between 0.001% w/w to 0.15% w/w. In other embodiments, the concentration of compounds 1, 2, 3, 4, 5, 6 or 7 or pharmaceutically acceptable salt thereof within the composition is between 0.01% w/w to 0.15% w/w. In other embodiments, the concentration of compounds 1, 2, 3, 4, 5, 6 or 7 or pharmaceutically acceptable salt thereof within the composition is between 0.01% w/w to 0.5% w/w. In other embodiments, the concentration of compounds 1, 2, 3, 4, 5, 6 or 7 or pharmaceutically acceptable salt thereof within the composition is between 0.01% w/w to 1% w/w.

The active compound for use according to the invention may be provided in any form suitable for the intended administration. Suitable forms include pharmaceutically acceptable salts, and pre- or prodrug forms of the compound of the invention.

A "salt thereof" is a salt of the instant compound which has been modified by making acid or base salts of the compound. The term "pharmaceutically acceptable salt" in this respect, refers to the relatively non-toxic, inorganic and organic acid or base addition salts of compound of the present invention suitable for pharmaceutical use. Pharmaceutically acceptable salts may be formed by procedures well known and described in the art. One means of preparing such a salt is by treating a compound of the present invention with an inorganic base.

Examples of acid addition salts of the compound of the present invention include, but is not limited to, the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. In certain embodiments, pridopidine is a pharmaceutically acceptable salt, such as the HCl salt or tartrate salt. Preferably, in any embodiments of the invention as described herein, the pridopidine is in the form of its hydrochloride salt.

As used herein, an "amount" or "dose" of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine in a preparation is 90 mg, regardless of the form of the preparation. Thus, when in the form of a salt, e.g. pridopidine hydrochloride, the weight of the salt form necessary to provide a dose of 90 mg pridopidine would be greater than 90 mg due to the presence of the salt.

As used herein, a "unit dose", "unit doses" and "unit dosage form(s)" mean a single drug administration entity/entities. A "unit dose", "unit doses" and "unit dosage form(s)" can be prepared for oral dosage forms, such as tablets, capsules, pills, powders, and granules.

As used herein, "about" in the context of a numerical value or range means 90-110% of the numerical value or range recited or claimed.

"Administering to the subject" or "administering to the (human) patient" means the giving of, dispensing of, or application of medicines, drugs, or remedies to a subject/patient to delay, relieve, cure, or reduce the symptoms associated with a condition, e.g., a pathological condition. Oral administration is one way of administering the instant compounds to the subject.

A compound according to the subject invention may be administered in the base form or in the form of pharmaceutically acceptable salts, preferably in a pharmaceutical composition together with one or more adjuvants, excipients, carriers, buffers, diluents, and/or other customary pharmaceutical auxiliaries.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compound to the subject.

The administration can be periodic administration. As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times weekly and so on, etc.

"Treat" or "treating" as used herein encompasses alleviating, lessening, reducing the severity of, eliminating or substantially eliminating, or ameliorating a physical, mental or emotional limitation in a subject afflicted with RTT. Treating also refers to delaying or prevention of symptoms or reduction of deficits associated with a disease.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a symptom of Rett Syndrome. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

It is understood that where a parameter range is provided, all integers within that range, and tenths thereof, are also provided by the invention. For example, "22 mg-300.0 mg" includes 22.0 mg, 22.1 mg, 22.2 mg, 22.3 mg, 22.4 mg, etc. up to 300.0 mg inclusive. This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: Evaluation of the Efficacy of Pridopidine in the Heterozygous MeCP2 Female Mouse Model of Rett Syndrome The goal of this study was to assess the effects of pridopidine in the female MeCP2-Het (BIRD) mouse model of Rett Syndrome (Guy 2001).

Materials:

Pridopidine (3 and 30 mg/kg) was administered orally twice daily (6 hours between dosing) at a dose volume of 10 ml/kg. On test days, pridopidine was administered 30 minutes prior to test.

Dosing commenced when mice were ~5.5 weeks of age and continued through the end of behavioral testing. Behavioral testing was done at 8 and 12 weeks of age.

Female MeCP2 (MeCP2_HET, Rett) mice and wild type (MeCP2_WT, WT) littermates were housed at 20-23° C. with 50% relative humidity, and a $^{12}/_{12}$ light/dark cycle. Chow and water were provided ad libitum. All tests were performed during the light phase. Animals were examined and weighed throughout the study to assure adequate health and suitability and to minimize non-specific stress associated with manipulation. All animals were examined and weighed prior to initiation and throughout the study to assure adequate health and suitability and to minimize nonspecific stress associated with manipulation. During the course of the study, $^{12}/_{12}$ light/dark cycle was maintained. The room temperature was maintained between 20 and 23° C. with a relative humidity maintained around 50%. Chow and water was provided ad libitum for the duration of the study. The tests were performed during the animal's light cycle phase.

Methods:

Treatment Groups:

WT mice—vehicle (subcutaneous once weekly, saline), n=24

Rett HET MeCP2 mice—vehicle (subcutaneous once weekly, saline), n=24

Rett HET MeCP2 mice—Pridopidine (3 mg/kg; orally twice daily), n=20

Rett HET MeCP2 mice—Pridopidine (30 mg/kg; orally twice daily), n=20

Behavioral Tests:
(I) Gait Analysis Using NeuroCube® System

The NeuroCube® system is a platform that employs computer vision to detect changes in gait geometry and gait dynamics in rodent models of neurological disorders, pain & neuropathies.

This platform is unique for gait testing for the following reasons:
- It is completely automated and thus removes any bias or subjectivity
- This system captures both gait geometry and gait dynamics (stance, swing, propulsion, etc.)

Mice were placed in the NeuroCube for a 5 min test. The most dominant of the features collected that define the disease phenotype (symptom descriptors) was identified and ranked. Complex bioinformatic algorithms were employed to calculate the discrimination probability between the WT and the Rett HET MeCP2 mice and detect a test compound's ability to reverse the disease phenotype. Discriminations between mutant and wild type was calculated as well as the recovery of disease features in Rett HET MeCP2 mice treated with the test compound.

(2) Clasping

Clasping is used to assess muscular strength in limb muscles. Mice were held by the tail and gently lifted until the front paws just lift off the counter surface. The experimenter observed the legs and determined clasping or splaying of limbs. After testing, animals were placed back into the test or home cage. Percent clasping of the hindlimbs was determined and reported.

(3) Startle Response. Prepulse Inhibition (PPI)

The acoustic startle measures an unconditioned reflex response to external auditory stimulation. Prepulse inhibition (PPI) consisting of an inhibited startle response (reduction in amplitude) to an auditory stimulation following the presentation of a weak auditory stimulus or prepulse, has been used as a tool for the assessment of deficiencies in sensory-motor gating, such as those seen in schizophrenia. This is an optional test that would only be performed on those animals that do not exhibit audiogenic seizures.

Mice were placed in the PPI chambers (Med Associates) for a 5 min session of white noise (70 dB) habituation. After the acclimation period the test session automatically started. The session started with a habituation block of 6 presentations of the startle stimulus alone, followed by 10 PPI blocks of 6 different types of trials.

Trial types were: null (no stimuli), startle (120 dB), startle plus prepulse (4, 8 and 12 dB over background noise i.e. 74, 78 or 82 dB) and prepulse alone (82 dB). Trial types were presented at random within each block. Each trial started with a 50 ms null period during which baseline movements were recorded. There was a subsequent 20 ms period during which prepulse stimuli were presented and responses to the prepulse were measured. After further 100 ms the startle stimuli were presented for 40 ms and responses recorded for 100 ms from startle onset. Responses were sampled every millisecond. The inter-trial interval was variable with an average of 15 s (range from 10 to 20 s).

In startle alone trials the basic auditory startle was measured and in prepulse plus startle trials the amount of inhibition of the normal startle was determined and expressed as a percentage of the basic startle response (from startle alone trials), excluding the startle response of the first habituation block.

Brain Collection:

After all behavioral testing was completed brain samples were collected 60 minutes after dosing with pridopidine. Mice were euthanized via cervical dislocation and decapitated. From 10 mice/treatment group, whole brains were collected, weighed, and then frozen on dry ice. Samples were stored at −80° C. until analysis of brain-derived neurotrophic factor (BDNF).

Bdnf Analysis:
Total RNA Extraction:

Tissues (whole brain) were homogenized, and RNA extracted. 2×1 min at 25 Hz in 750 µL of QIAzol Lysis Reagent (Cat #79306, Qiagen, Valencia, CA) with Tissue-Lyser (Qiagen, Valencia, CA) and 5 mm stainless steel beads (Cat #69989, Qiagen, Valencia, CA). Once tissues were disrupted, samples were allowed to incubate at room temperate for 5 minutes.

For RNA extraction, manufacturer protocol for RNeasy 96 Universal Tissue Kit (Cat #74881, Qiagen, Valencia, CA) for RNA isolation was followed. Briefly, 150 µL of Chloroform (Cat #C2432, Sigma-Aldrich, St. Louis, MO) was added and samples were shaken vigorously for 15 seconds followed by 3-minute incubation at room temperature. The aqueous phase was separated from the organic phase by centrifugation at 6,000×g (Beckman Coulter Avanti J-30I), 4° C. for 15 minutes. The aqueous phase was then transferred to a new 96-well block and total RNA was precipitated with equal volume of 70% ethanol. Content was transferred to an RNeasy 96-well plate, followed by centrifuge at 6,000-x g (Beckman Coulter Avanti J-30I), at room temperate for 4 minutes. Total RNA bound to column membranes was treated with RNase-Free DNase set (Cat #79254, Qiagen, Valencia, CA) for 30 minutes, followed by 3 washing steps with RW1 and RPE buffers (provided with RNeasy 96 Universal Tissue Kit). RNA was eluted with RNase-Free water.

Total RNA Quantification and Reverse Transcription:

Samples were quantified using NanoDrop 8000 (Thermo Scientific). One microgram of total RNA was reverse transcribed into cDNA with 3.2 µg random hexamers (Cat #11034731001, Roche *Applied Science*, Indianapolis, IN), 1 mM each dNTP (Cat #11814362001), Roche *Applied Science*, Indianapolis, IN), 20U Protector RNase Inhibitor (Cat #03335402001, Roche *Applied Science*, Indianapolis, IN), 1X Transcriptor Reverse Transcription reaction buffer and IOU Transcriptor Reverse Transcriptase (Cat #03531287001, Roche *Applied Science*, Indianapolis, IN) in 20 µL total volume.

Up to three independent RT reactions were performed for each RNA sample. The reactions were allowed to proceed at room temperature for 10 minutes, 55° C. for 30 minutes, and then inactivated at 85° C. for 5 minutes in GeneAmp PCR Systems 9700 thermal cycler (*Applied Biosystems*, Foster City, CA). cDNA samples were diluted 10 folds with RNase-Free water for qPCR analysis.

Tissues (whole brain) were homogenized, and RNA extracted and quantified. One microgram of total RNA was reverse transcribed to create cDNA for quantitative PCR (qPCR). qPCR was performed using the primers detailed in Table 4 below.

For all reactions utilizing Universal Probe Library Probes, 5 µl of the diluted cDNA was amplified with 12.5 µL 2× FastStart Universal Probe Master Rox (Cat #04914058001, Roche *Applied Science*, Indianapolis, IN), 0.5 µL Universal Probe Library Probe (Roche *Applied Science*, Indianapolis, IN), 200 nM of gene specific primer—HPLC purified (Sigma-Aldrich, St. Louis, MO) in 25 µL reaction volume. The reactions were run on the ABI 7900HT Sequence Detection System (*Applied Biosystems*, Foster City, CA). qCPR conditions were 95° C. for 10 minutes for activation of FastStart Taq DNA Polymerase followed by 40 cycles of 95° C. for 15 seconds and 60° C. for 1 minute. For primers and Universal Probe Library used forqgPCR please refer to Table 4 below.

Statistical Analysis:

Data from standard tests were analyzed by genotype (t-test) and by treatment (ANOVA) followed by post-hoc comparisons where appropriate. For some measures,

TABLE 4 qPCR and primers/probe information

| Mouse Gene ID | 5' Primer Sequence | 3' Primer Sequence | Universal Probe Library # | Tissue | PCR Efficiency |
|---|---|---|---|---|---|
| ATP5B | GGCACAATGCAGGAAAGG (SEQ ID NO: 1) | TCAGCAGGCACATAGATAGCC (SEQ ID NO: 2) | 77 | Brain | 1.89 |
| RPL13A | TTGTGGCCAAGCAGGTACT (SEQ ID NO: 3) | GTTGATGCCTTCACAGCGTA (SEQ ID NO: 4) | 77 | Brain | 1.91 |
| GAPDH | CAATGTGTCCGTCGTGGATCT (SEQ ID NO: 5) | GTCCTCAGTGTAGCCCAAGATG (SEQ ID NO: 6) | N/A | Brain | 1.87 |
| BDNF1 | AGTCTCCAGGACAGCAAAGC (SEQ ID NO: 7) | TGCAACCGAAGTATGAAATAACC (SEQ ID NO: 8) | 31 | Brain | 2.00 |
| BDNFIV | GCTGCCTTGATGTTTACTTTGA (SEQ ID NO: 9) | AAGGATGGTCATCACTCTTCTCA (SEQ ID NO: 10) | 31 | Brain | 2.04 |
| BDNFVI | CCGAGAGCTTTGTGTGGAC (SEQ ID NO: 11) | TCATGCAACCGAAGTATGAAA (SEQ ID NO: 12) | 31 | Brain | 1.93 |
| BDNFIX | GCCTTTGGAGCCTCCTCTAC (SEQ ID NO: 13) | GCGGCATCCAGGTAATTTT (SEQ ID NO: 14) | 67 | Brain | 2.01 | qPCR Data Analysis:

Whole brain cDNA prepared from a pooled sample of WT vehicle treated animals was used as calibrator (calibrator is diluted same as sample cDNA) to normalized plate-to-plate variations. See Table 3 above for PCR efficiencies of the qPCR assays used in this study.

Each cDNA sample (diluted 1:10) was assayed in triplicates and the Ct values averaged. Values that lie greater than 0.5 standard deviation of the average were discarded.

Relative quantity of the PCR product (relative to the calibrator) was calculated as follows:

Relative Quantity of Target gene =
$(PCR\ Efficiency Target)^{(Ctcalibrator-Ctsample)}$ Relative Quantity of Housekeeping Gene 1 =
$(PCR\ Efficiency housekeeping1)^{(Ctcalibrator-Ctsample)}$ Relative Quantity of Housekeeping Gene 2 =
$(PCR\ Efficiency housekeeping2)^{(Ctcalibrator-Ctsample)}$ Relative Quantity of Housekeeping Gene 3 =
$(PCR\ Efficiency housekeeping3)^{(Ctcalibrator-Ctsample)}$ Geometric mean for the three housekeeping genes was calculated as follows:

Geometric mean=(relative quantity of housekeeping gene 1*relative quantity of housekeeping gene 2*relative quantity of housekeeping gene 3)$^{(1/3)}$ Relative level of target gene was calculated as follows:

Relative Quantity of Target gene÷Geometric mean of housekeeping genes

Relative level of target gene was then normalized to the WT vehicle group.

repeated-measures ANOVAs were performed. For clasping data, N-1 two-proportional tests were performed. An effect was considered significant if p<0.05. All data are represented as the mean and standard error to the mean (s.e.m). Values ±2 standard deviations from the mean were considered outliers.

Data Analysis from NeuroCube:

The output of NeuroCube is a set of dozens of behavioral features that are submitted for analysis with machine learning techniques used in bioinformatics. Many of these features are correlated (e.g. rearing counts and supported rearing counts). Therefore, PGI forms statistically independent combinations of the original features (further referred to as de-correlated features) that discriminate between the two groups more effectively.

Each de-correlated feature extracts information from the whole cluster of the original features, so the new feature space has lower dimensionality. Next, PGI applies a proprietary feature ranking algorithm to score each feature's discrimination power (ability to separate the two groups, e.g. control and disease).

Ranking is an important part of the analyses because it weighs each feature change by its relevance: if there is a significant change in some irrelevant feature measured for a particular phenotype, the low rank of this feature will automatically reduce the effect of such change in the analyses, so there is no need to resort to the conventional "feature selection" approach and discard information buried in the less informative features. Ranking algorithm can be applied to either original or the new features to gain insight about the key control-disease differences.

Feature Analysis: Quantitative Assessment of Disease Phenotype

In the new feature space, the overlap between the "clouds" (Gaussian distributions approximating the groups of mice in the ranked de-correlated features space) serves as a quantitative measure of separability ("distinguishability") between the two groups. For visualization purposes, each cloud was plotted with its semi-axes equal to the one standard deviation along the corresponding dimensions.

Figure 2:
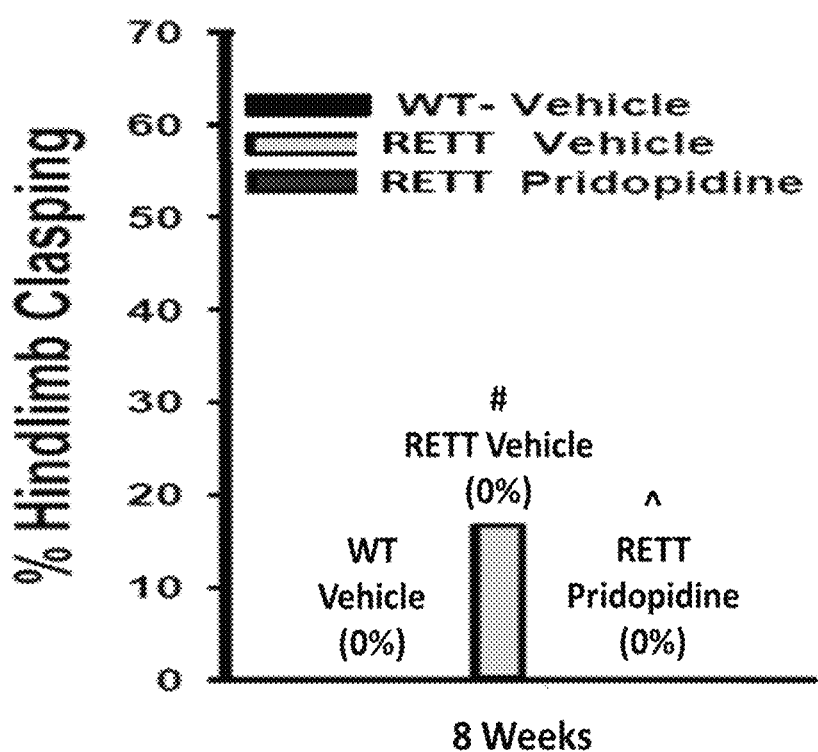
FIG. 2: Percentage of mice showing hindlimb clasping. Hindlimb clasping is measured in mice held by the tail and gently lifted until the front paws just lift off the counter surface. The experimenter observed the legs and determined clasping or splaying of limbs. WT mice show no clasping at 8 weeks of age (0%). Rett mice (MECP2 heterozygous, "RETT" mice) show significant clasping at 8 weeks of age (#p<0.05 vs. placebo). Rett mice ("RETT") treated with pridopidine (30 mg/kg) show rescue (i.e. no clasping, 0%) at 8 weeks, ^p<0.06 compared to RETT-vehicle group. Source: DPR-2016-061

Results:

In FIG. 2 the black column represents vehicle treated WT animals, the light gray column represents vehicle treated Rett animals, the darker gray column represents pridopidine treated Rett animals (30 mg/kg).

Figure 3:
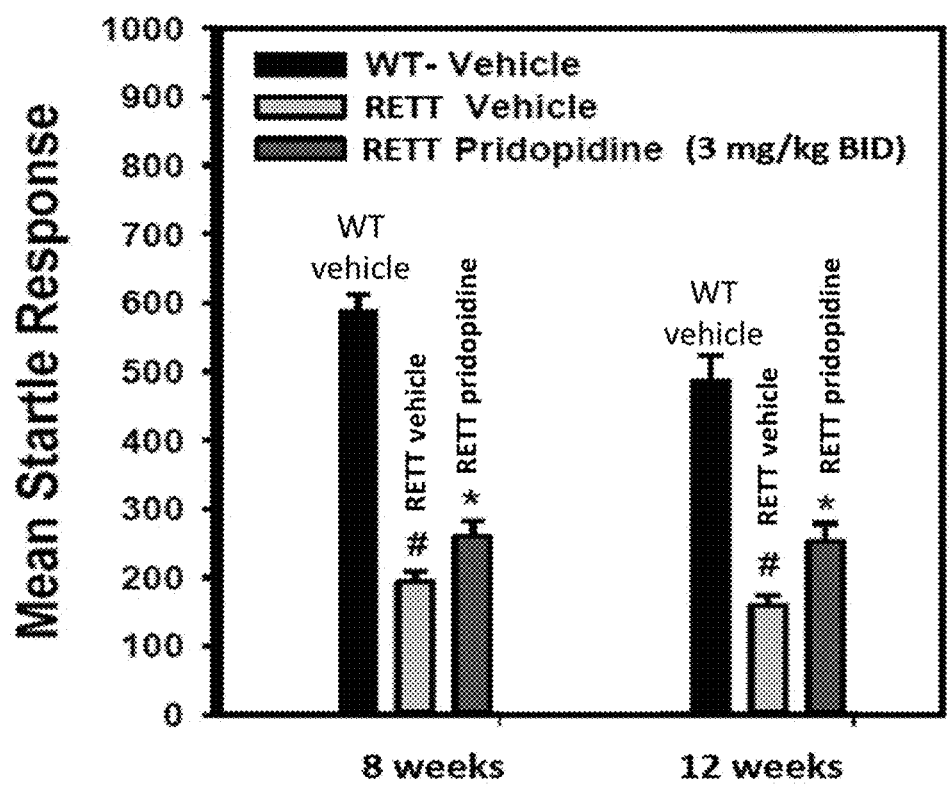
FIG. 3: Pridopidine improves mean startle response in response to acoustic stimuli in RETT mice at 8 and 12 weeks of age. The acoustic startle is measured by placing mice in a sound-attenuated startle chamber which measures the force of the movements made by the mouse. The amount of inhibition following an acoustic prepulse is expressed as a percentage of the basic startle response (from startle alone trials), excluding the startle response of the first habituation block. Data are expressed as mean±SEM. #p<0.05 compared to WT-vehicle group. *p<0.05 compared to Rett-vehicle group

In FIG. 3 the black columns to the left represent vehicle treated WT animals, the light gray columns represent vehicle treated Rett animals, the darker gray columns represent pridopidine treated Rett animals (3 mg/kg).

Behavioral Tests:

(1) Clasping

Rett Syndrome patients lose or fail to acquire purposeful hand movements, and these are replaced by stereotypical movements such as hand wringing. In the Rett mouse model, this symptom correlates with a hindlimb clasping phenotype. Rett model mice show significantly more clasping compared to the WT mice (FIG. 2). Pridopidine improves clasping at 8 weeks as shown in FIG. 2. Vehicle-treated RETT mice show significantly more clasping compared to the WT mice. Pridopidine (30 mg/kg bid) normalizeS this behavior (p<0.06) at 8 weeks. At 8 weeks, columns representing the WT vehicle treated and pridopidine treated (30 mg.kg) animals are zero. This suggests that pridopidine 30 mg/kg is efficacious for treating this symptom, and may delay its onset.

(2) Startle Response/PPI

Rett Syndrome symptoms reduced alertness and attention span are recapitulated in the mouse model and assessed using the acoustic startle response. Pridopidine has a significant beneficial effect on the startle response as shown in FIG. 3. Vehicle-treated Rett mice startled less compared to vehicle-treated WT mice. Pridopidine (3 mg/kg bid) improves the startle response in Rett mice at both 8 and 12 weeks of age.

(3) NeuroCube®

The discrimination probability between WT and Rett mice at 8 and 12 weeks of age was 90% and 94%, respectively. Some of the top gait features that discriminated between WT and Rett include longer stride and step length, narrower base width, and less paw intensity of WT mice compared to Rett mice.

Figure 4:
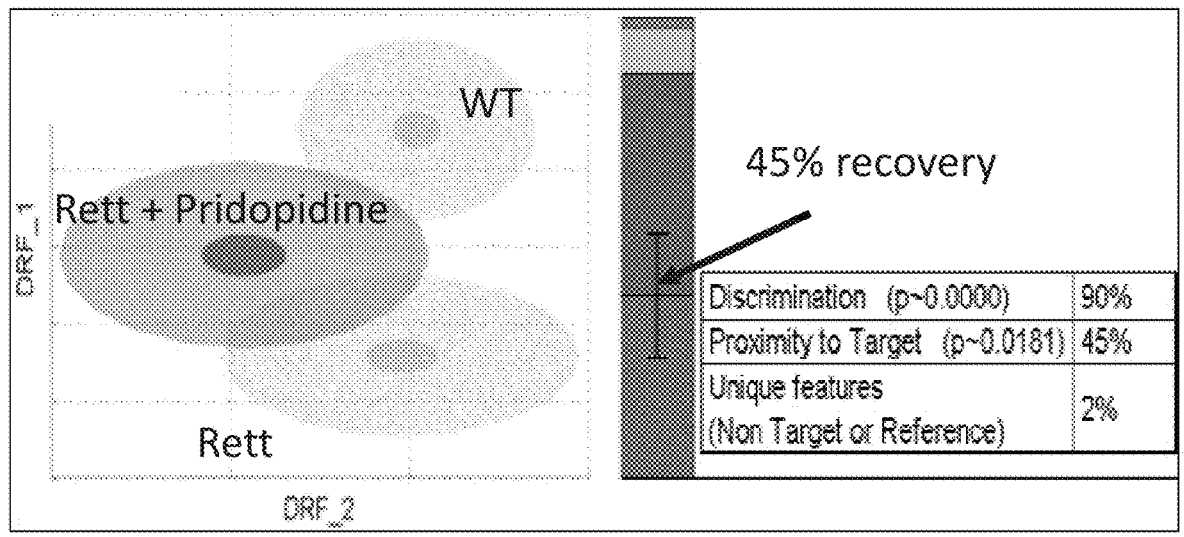
FIG. 4: Summary of recovery analysis of gait features in female Rett model mice by Pridopidine (30 mg/kg) at 8 weeks of age. Pridopidine shows significantly improvement in gait in Rett mice by 45% (p=0.0181) (darkest color) at 8 weeks. The cloud graphs are used to visualize WT (upper cloud), Rett female mice (lower right-most cloud), and Rett female mice+pridopidine (lower-left most cloud) relationship in the optimal discrimination feature space.
Figure 5:
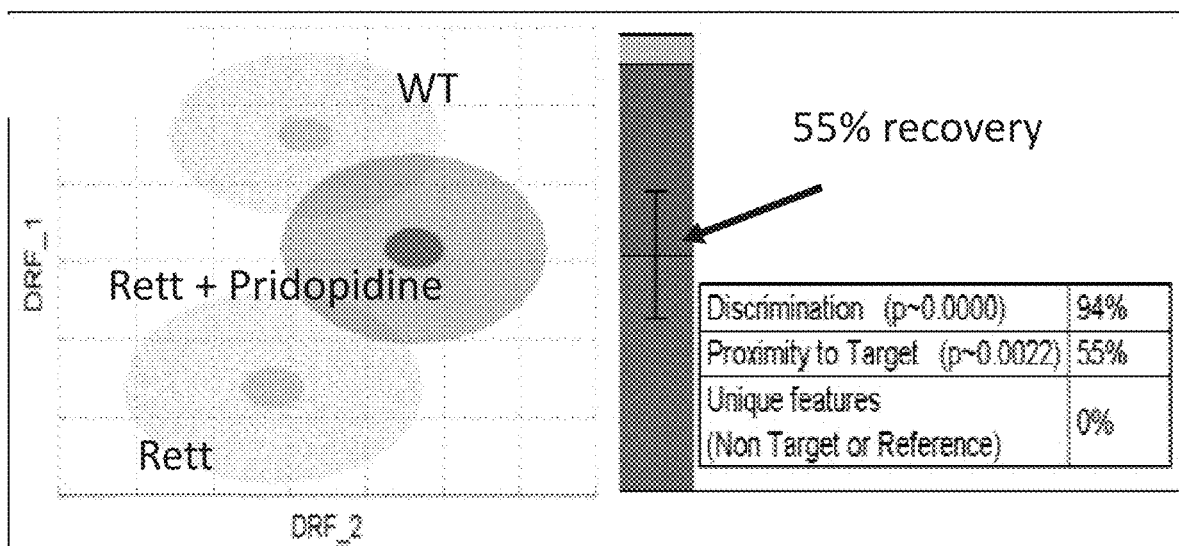
FIG. 5: Summary of recovery analysis of gait features in Rett female mice by Pridopidine (30 mg/kg) at 12 weeks of age. The bar graphs show pridopidine significantly improved gait in Rett mice by 55% (p=0.0022) (darkest color) at 12 weeks. The cloud graphs are used to visualize WT (upper cloud), Rett mice (lower left-most cloud), and Rett+pridopidine (lower-right most cloud) relationship in the optimal discrimination feature space.

The effects of pridopidine on gait performance at 8 weeks are shown in FIG. 4. The effects of pridopidine on gait performance at 12 weeks are shown in FIG. 5. Pridopidine (30 mg/kg) shows significant recovery of overall gait features at 8 weeks and 12 weeks (45% and 55%, respectively).

Further analysis shows significant differences in specific gait domains as shown in Table 4 below. The Rett mice were significantly different from the WT control mice overall, in all gait features. Week 8 data show that pridopidine (3 and 30 mg/kg BID) improves body motion and gait alone in Rett mice. Pridopidine treatment (3 mg/kg) significantly improves gait alone and body motion at 12 weeks. Significant effects on gait alone, body motion and paw positioning are also seen with pridopidine (30 mg/kg BID) at 12 weeks.

TABLE 5

Effects of pridopidine on gait at 8 and 12 weeks.

| | Feature | % Discrimination WT vs MeCP2-Het | % Recovery 3 mg/kg BID | % Recovery 30 mg/kg BID |
|---|---|---|---|---|
| 8 weeks | Gait | 92%, p = 0 | 38%, p = 0.022 | 71%, p = 0.004 |
| | Body Motion | 79%, p = 0.001 | 81%, p = 0.003 | 84%, p = 0.01 |
| 12 weeks | Gait | 94%, p = 0 | 60%, p = 0.005 | 100%, p = 0 |
| | Body Motion | 83%, p = 0 | 65%, p = 0.021 | 59%, p-0.041 |
| | Paw Positioning | 87%, p = 0.001 | 35%, p = 0.192 | 52%, p = 0.032 |

BDNF Analysis

The effects of pridopidine on relative BDNF expression in brain samples of the WT and Rett mice are shown in FIGS. 6-10.

Figure 6A:
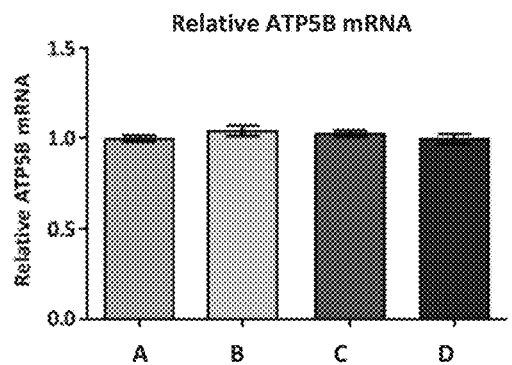
Figure 6B:
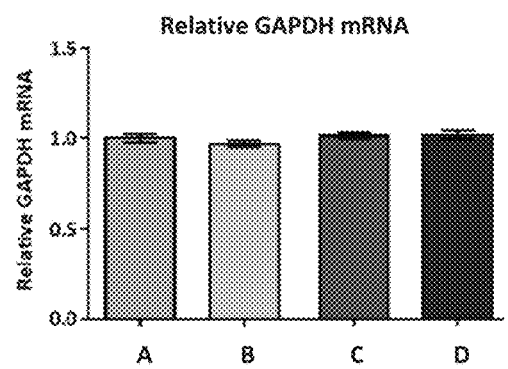
Figure 6C:
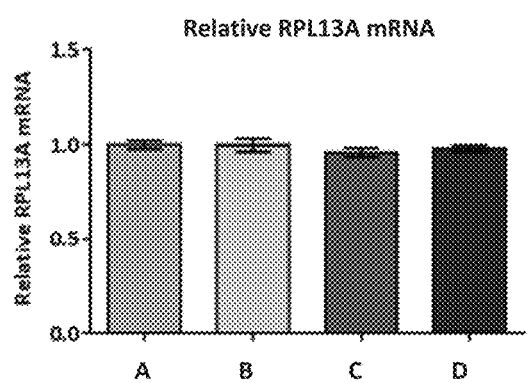
Figure 9A:
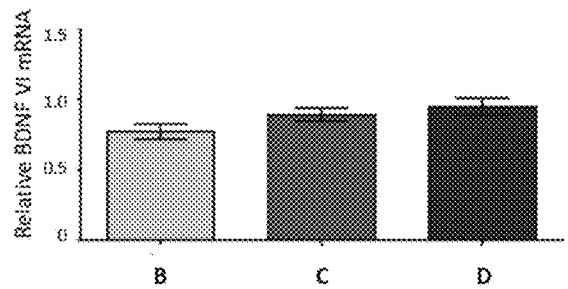
Figure 9B:
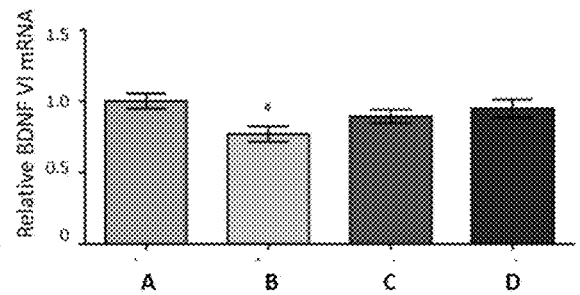
Figure 10A:
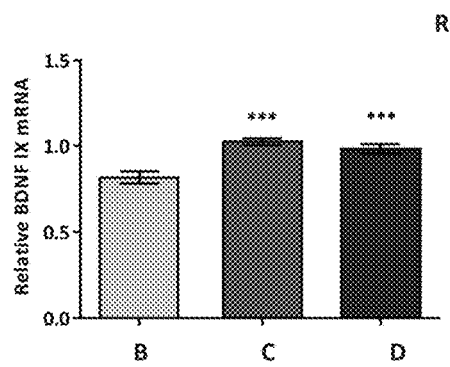
Figure 10B:
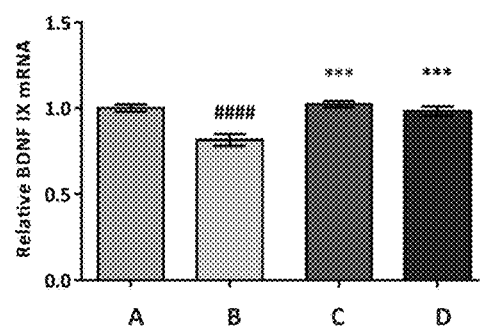

Whole brain control housekeeping genes mRNA expression levels do not change between the different animal groups treatments examined (see FIGS. 6A-6C).

As compared with WT (vehicle), BDNF I mRNA expression is significantly decreased in Rett (vehicle) treated group. Pridopidine treatment (3 or 30 mg/kg) does not affect levels of BDNF I mRNA in Rett mice (see FIGS. 7A-7B).

As compared with WT (vehicle), BDNF IV mRNA expression is significantly decreased in Rett (vehicle) treated group. Pridopidine treatment (3 or 30 mg/kg) rescues downregulated BDNF IV mRNA in Rett mice close to WT levels (see FIGS. 8A-8B).

As compared with WT (vehicle), BDNF VI mRNA expression was significantly decreased in Rett (vehicle) treated group. Pridopidine treatment (3 or 30 mg/kg) does not affect levels of BDNF VI mRNA in Rett mice (see FIG. 9).

As compared with MeCP2_WT (vehicle), BDNF VI mRNA expression was significant decreased in McCP2_HET (vehicle) treated group. No significant changes were observed in the McCP2_HET treated groups as compared with MeCP2_HET vehicle treated group (see FIG. 13).

As compared with WT (vehicle), BDNF IX mRNA expression is significantly decreased in Rett (vehicle) treated group. Pridopidine treatment (3 or 30 mg/kg) rescues downregulated BDNF IX mRNA in Rett mice close toWT levels (see FIGS. 10A-10B).

Conclusion

This study evaluated the effects of chronic subcutaneous administration of pridopidine on gait, hindlimb clasping, and startle/PPI in Rett model mice.

Pridopidine (3 mg/kg BID) differs significantly from vehicle-treated Rett mice in gait measures. Additionally, Rett mice treated with pridopidine (3 mg/kg BID) show increased startle response compared to vehicle-treated HET mice. Rett mice treated with pridopidine (30 mg/kg BID) show significant recovery of gait features and normalized clasping at 8 weeks of age.

Treatment with both doses of Pridopidine (3 and 30 mg/kg BID) fully rescues the downregulated mRNA levels of BDNF IV and BDNF IX. A Positive effect of Pridopidine on expression of BDNF mRNA is consistent with improvement observed in behavioral paradigms.

Example 2: RNA Analysis of Pridopidine Treated MeCP2 Mice

Methods:

Female Rett model mice (MeCP2 Heterozygotes) and wild type (WT) littermates at ~4.5 weeks of age were treated with either pridopidine or vehicle. Pridopidine (3 and 30 mg/kg) was administered orally twice daily (6 hours between dosing) at a dose volume of 10 ml/kg. There were four treatment groups: 1. WT mice—vehicle, 2. Rett mice—vehicle, 3. Rett mice—Pridopidine (3 mg/kg; PO twice daily), 4. Rett mice—Pridopidine (30 mg/kg; PO twice daily).

RNA was isolated from striatum and cortex of the pridopidine treated and vehicle treated mice. Next, RNAaseq was performed using the Illumina TruSeq Stranded mRNA Kit. with HiSeq 2×50nt paired end sequencing. Fastq files were downloaded, and Star aligner with GRCm38 primary assembly annotation and standard options was used to align the fastq files. Genes were counted with FeatureCounts on GeneCode vM7. For feature_type and group_by, "gene" was used and "reverse" was used for strandedness. Merging of read counts into a single matrix and all other downstream computational processing was done and will be done in R statistical programming language. Plots showing the first and second principal component of the samples were used to select outliers. Transcripts that had less than 10 reads per gene on average were filtered out. CalcNormFactors from the edgeR R package was used to normalize the counts via the TMM method. The limma R-package was used to transform and model the gene-level quantification data. limma::voom was used to transform the count data to log 2-counts per million and calculate the mean-variance relationship.

For yet to be completed differential expression analysis, limma::lmFit is used to fit a linear model for each gene based on the experimental design matrix and with an added term to correct for batch information. limma::eBayes is used to calculate the empirical Bayes moderated t-statistic for contrast significance. Multiple hypothesis adjusted p-values ise calculated using limma::toptable, which implemented the Benjamini-Hochberg procedure to control FDR. Differential expression contrasts between untreated MeCP2 HET and untreated WT samples, treated MeCP2 HET and untreated MeCP2 HET samples, will be independently calculated for all three tissues. To test whether the treatment gene expression signature is enriched for relevant biological signatures, Gene Set Enrichment Analysis-(GSEA) is used. Genes are ranked by limma generated t-statistic for a given contrast. Enrichr is used for pathway analysis.

This experiment assessed whether pridopidine reverses aberrant transcription observed in the Rett mice. This was done by testing whether pridopidine restores the expression of genes perturbed in disease context back to WT levels. Additionally, the impact of pridopidine on gene expression in the Rett Syndrome mouse model was assessed.

Results:

Pridopidine reverses Rett syndrome disease gene expression signature in the striatum and cortex analyzed by the Gene Set Enrichment Analysis (GSEA) method

TABLE 6

Pridopidine reversal of gene expression signal in the striatum of Rett model mice

| Dose | Direction | Adj p value | Statistical test |
|---|---|---|---|
| 3 mg/kg BID | Down in Rett | 2.40E−04 | GSEA |
| 30 mg/kg BID | Up with Prido | 1.87E−03 | GSEA |

TABLE 7

Pridopidine reversal of gene expression signal in cortex of Rett model mice

| Dose | Direction | Adj p value | Statistical test |
|---|---|---|---|
| 3 mg/kg BID | Down in Rett | 2.71E−02 | GSEA |
| 30 mg/kg BID | Up with Prido | 6.20E−04 | GSEA |
| 3 mg/kg BID | Up in Rett | 7.66E−03 | GSEA |
| 30 mg/kg BID | Down with Prido | 4.26E−04 | GSEA |

Comparison of broad gene expression patterns reveals that pridopidine strongly reverses the gene expression pattern in both the striatum and cortex of Rett mice.

TABLE 8

Pridopidine reversal of Rett disease genes in the striatum

| Geneset | Dose | NES | p.value | p.adjust | LeadingEdge |
|---|---|---|---|---|---|
| Up with Prido Down in Rett | 3 mg/kg BID | −2.50 | 1.90E−04 | 2.40E−04 | MAP3K6\|ESR2\|XIRP2\|BHLHE22\|SGK1\|NEUROD1\|BGLAP\|SLC9A3\|APOL6\|FAM19A1\|NPSR1\|SIDT1\|PLEKHF1\|OTOG\|VIP\|CLDN22\|RTN4R\|MEDAG\|ARSI\|MUC2\|PTPN3\|IRX2\|ADAM33\|GATA3\|PRDM8\|WISP2\|C12orf50\|SLC9A4\|SIX4\|TMEM215\|PMCH\|CD200R1L\|HKDC1\|CBLN4\|MPL\|SAMD7\|WNT9A\|LRRC17\|HCRT\|ADRA1D\|SLC17A6\|OXT\|ZP2\|CDHR2\|ALOX12B\|CHRNB3\|PLCXD2\|GRM2\|ADRA1B\|TMEM145\|TSPAN11\|NPR3\|KCNK4\|TEX40\|SCXB\|NHLH2\|AMDHD1\|PTGDR\|WNT6\|C1R\|ADCYAP1\|ZNF648\|SEC14L4\|KCNAB3\|ALDH3A1\|CHRNA6\|SYTL1\|PDZK1IP\|ETNK2\|PLG\|HES3\|NEB |
| Down with Prido Up in Rett | 3 mg/kg BID | 2.18 | 2.11E−04 | 2.40E−04 | DKK2\|L3MBTL4\|PHEX\|KLHL10\|CLSPN\|CHST4\|GALR1\|LACTBL1\|F9\|CLDN23\|CCR2\|SLC10A4\|RXRG\|ARID3C\|SLC26A5\|CD300LG\|SLFN12L\|FGF3\|CHAT\|GPX6\|CXCL10\|ANXA10\|PTPN7\|LHX8\|FXYD3\|NEUROG1\|TMPRSS11A\|MYCT1\|ZBP1\|F2RL1\|DCST1\|NKX2-1\|NRI3\|CNR2\|GPR139\|MYBPH\|CHRNB4\|PRSS56\|SYT15\|RYR1\|STYK1\|EDN1\|ALAS2\|OSM\|PROKR1\|SEC14L3\|ZNF616\|NXF3\|TACR1 |
| Up with Prido Down in Rett | 30 mg/kg BID | −1.77 | 1.93E−04 | 1.87E−03 | SPEM1\|ESR2\|ARC\|SGK1\|SP5\|KLHL35\|GRAP2\|FPR2\|TMPRSS6\|C11orf96\|BTG2\|SNX31\|MC3R\|GLIS1\|LTB\|FMO2\|GC\|TFAP2B\|DEFB130\|TECTA\|CKM\|SLC25A25\|FGA\|FOSL2\|CEBPD\|CH25H\|C6orf229\|C6orf163\|AOAH\|CHIA\|MIDN\|CALCB\|ZP2\|SSUH2\|GBX1\|SAP25\|TRIM29\|NEUROD4\|MGST2\|ITK\|HAAO\|GUCY2C\|CNGA3\|MAFA\|FAM83G\|APOLD1\|C17orf50\|PAX5\|C2orf74\|SYTL1\|PDZK1IP1\|PLG\|PCSK9\|CRLF1 |

Table 8 shows that pridopidine 3 mg/kg BID reverses the Rett gene expression pattern in the striatum in both directions (upregulates genes that are down in Rett mice vs WT and down regulates genes that are up in Rett mice vs WT). Pridopidine 30 mg/kg BID significantly upregulated genes that are down in Rett mice vs WT.

in both directions (upregulates genes that are down in Rett mice vs WT and down regulates genes that are up in Rett mice vs WT).

The effect of pridopidine on the expression of genes downstream to the BDNF-TrkB pathway was assessed.

TABLE 9

Pridopidine reversal of Rett disease genes in the Cortex

| Geneset | Dose | NES | p.value | p.adjust | LeadingEdge |
|---|---|---|---|---|---|
| Prido Up Rett Down | 3 mg/kg BID | −1.477 | 2.30E−03 | 7.66E−03 | NLRP10|CRABP1|ZAR1|CD300E|STK32B|MS4A15|CASR|MPZ| OPRM1|ATN1|GC|C11orf85|STOML3|STK31|C10orf53|GHSR|RHCG| MC4R|CYP19A1|C9orf171|CYP4A22|COL6A5|INSL6|PPM1J|S100A8| HLAA|SLC22A2|GPAT2|HP|CCDC170|PADI1|NMRK2|BRS3|SP110| TMEM252|TFAP2C|LSMEM2|TFPI2|OXGR1|SLC6A3|CCDC67| FSCN2|SLC38A8|CHRNB4|TMEM174|TMPRSS11A|SCN11A|GDPD4| CCDC38|SLC24A1|GNB3|MXD3|SPEM1|AIRE|ATF3|TAF7L |
| Prido Down Rett Up | 3 mg.kg BID | 1.356 | 1.09E−02 | 2.71E−02 | CBLN2|AKAP2|PTPRQ|ALAS2|MEDAG|ATOH7|GGT6|ARMC4| TSHZ3|PATL2|TMEM88|TRABD2B|GALNT9|DNAJC21|SLCO1B3|ANXA11| CXCL6|MKX|XIRP2|TMEM30B|RXFP1|SGK494|AKR1C3|C4orf22| C3orf80|TMEM178A|LDB2|CD7|ADCY10|EMILIN3|CHRNA5| ADRA1D|GLT8D2|OSBPL1A|F2RL2|PAMR1|AMDHD1|ZBP1|CUZD1| DKK3|MYBPC1|SYCE1L|C14orf39|GFRA2|FEZF2|HIST2H2BF|CCBE1| GCNT4|VGLL3|MBOAT4|CA10|KIAA0226L|SERINC2|MYLK3|PKD1L2| FHOD3|HS3ST2|ABRA|EXPH5|CHRNA1|FAM132B|TMEM232| SATB2|BMP8A|BMP3|B3GNT8|SERPINB8|COL12A1|SLC9B2|KRT80| NEUROD6|ADRA1B|CCDC129|PPARG|FIGF|ZNF296|TRPV6|LAYN| ZBTB18|TSKS|NPC1L1|FAP|NTN5|MICAL2|CLDN23|TBX22|KRT7| DNAH14|PSRC1|ARHGAP25|PRDM8|OVOL2|PABPC4L|C8orf46| HERC6|C1QL3|HOPX|MAGIX|DDIT4L|SLC26A4|IRGC|TSPAN11| ADAM18|GKN1|CHRNB3|NKX3-1|ADRB3|VIP|IL12A|KIAA1522| C2CD4B|RTN4R|SYTL2 |
| Prido Up Rett Down | 30 mg/kg BID | −2.631 | 1.48E−04 | 4.26E−04 | EGR2|BSPRY| BAMBI|LEFTY2|CABYR|KCNE4|NGB|PAPOLB|RASL11A| FUT2|SPINK8|ZNI7189|ARL4D|DCN|LYVE1|SH2D6|C1orf198| RXFP3|GFAP|FOXR2|CBX2|ZAR1|FOSL2|MYO1A|USP51|STK32B| WNT2B|CASR|ICOSLG|CYBRD1|KLC3|FMO1|GDPD2|ATN1|CCL24| EFCAB1|C15orf48|CYR61|ELF4|NOV|GHSR|CEBPD|MC4R|MYOF| LGALS12|CKS1B|ITGBL1|ATOH8|ADAD2|MSH4|CYP19A1|CH25H| SLC2A4|TLR4|SCNN1A|ATP2C2|OTOF|NAB2|APOLD1|NR4A3|FLNC| CHRM4|DDIT4|ADAM21|ARID5A|KCNJ13|ASGR1|KNCN|C17orf98| KCNE2|NMRK2|EGR4|C17orf50|SLC6A20|NFKBIA|TMEM252| GATSL3|CHIA|IL1B|IGDCC3|CCNO|SPO11|ATRIP|OXGR1|LAT| SAMD14|COL13A1|FREM2|KRT77|WNK4|CCDC67|WFDC2|C2orf74| LGALS3|LTB|C10orf105|FGL1|TMPRSS11A|TOMM6|ADRA2A| MARCKSL1|NTSR1|DND1|SCN11A|SOX8|FZD2|PDZD3|OSR1|SOCS3| AMH|SLC24A1|EPS8L1|GNB3|KDM6B|MXD3|OXTR|ARHGAP9| SPEM1|MSANTD1|AIRE|DUSP9|LDOC1|ATF3|AMIGO3|TCFL5|PRKD2 |
| Prido Down Rett Up | 30 mg/kg BID | 2.081 | 3.10E−04 | 6.20E−04 | BMPER|BEND5|SDK1|SORCS3|TOX|DEPTOR|DPY19L1|FANCF| SKIDA1|CHAC1|PLCB4|PTGFRN|FGF22|CDS1|OSBPL3|CBLN2|RIMS3| AKAP2|RACGAP1|MEDAG|ZNF627|SORL1|CENPH|FGF23|GREB1| ATOH7|ASAP2|HIST1H4C|PATL2|TMEM88|PRICKLE1|NPNT|CMC2| FIGNL1|GALNT9|RASGEF1B|C11orf87|DNAJC21|HIST1H2BC| BACH2|CXCL6|PLXDC1|HIVEP1|TSPAN5|WEE1|KHDRBS3|IL17B| CD40|METTL18|AGTR1|C3orf80|SSTR4|COL15A1|CITED4|MAP10| LDB2|DYX1C1|FBXW7|HEBP2|ADCY10|PCDHA13|PRR15|PARVA| PCSK1|FSTL4|SLCO4C1|BST1|SLC35G1|ETV6|STOX1|HAPLN4| ADRA1D|ACSL5|CD300LG|PLCL2|PCDHA11|NRP1|LRRK2|B4GALNT3| ZBP1|PDIA5|C14orf39|FADD|GFRA2|ASPG|IQGAP2|NINJ2|ASAP1| GCNT4|SULF2|CDYL2|BOK|MBOAT4|PHF11|PKNOX1|MYOCD| COBL|TSSK4|PRSS23|MURC|FHOD3|HS3ST2 |

Table 9 shows that pridopidine at both 3 and 30 mg/kg BID reverses the Rett gene expression pattern in the cortex Pridopidine 30 mg/kg BID significantly increases the expression of genes downstream to BDNF (Table 10).

TABLE 10

Pridopidine increases expression of genes downstream to BDNF

| Dose | NES | p.value | p.adjust | LeadingEdge |
|---|---|---|---|---|
| 30 mg/kg BID | 1.752 | 3.04E−03 | 4.44E−03 | Nab2|Nr4a3|Egr2|Dusp5|Fos|Errfi1|Per2|Egr4|Nab1| Plk2|Gadd45g|Arc|Klf10|Klf5|Baz1a|Ier2|Ptger4|Cebpb| Egr1|Sertad1 |

Example 3: Pridopidine Improves Gait Function in Male MeCP2 Knock-Out (KO) Mouse Model of Rett Syndrome (Rett-KO)

Methods:

A colony of Rett model mice (Jackson Laboratories, Bar Harbor, ME; B6.129P2-Mecp2tm2Bird/J | Stock Number: 003890) was established by crossing heterozygous (het) females with wild type (WT) males (C57B1/6J). Heterozygous MeCP2 Rett model mice (Rett-KO) and their wild-type (WT) littermates were housed in a temperature-controlled room between 20 and 23° C. with 50% humidity and a 12/12 light/dark cycle. The room temperature was maintained between 20 and 23°C with a relative humidity maintained around 50%. Chow and water were provided ad libitum for the duration of the study. Additionally, upon initial observation of signs of hindlimb splay and/or locomotor difficulty, mice were provided with hydrogel daily. After weaning, mice were single housed in OPTImice cages. All animals remained single housed during the remainder of the study. Mice were balanced and assigned to treatment groups, using baseline body weight and grip strength measures prior to start of study. All tests were performed during the animal's light cycle phase.

Pridopidine was evaluated at 30 mg/kg BID. Compound was dissolved in sterile DDW and administered orally twice a day (BID) at a dose volume of 10 mL/kg.

NeuroCube®—Gait Analysis

The NeuroCube® (NRC) system is one of PsychoGenics' proprietary technologies. It is platform that employs computer vision to detect changes in gait geometry and gait dynamics in rodents. This platform is unique for gait testing for the following reasons:

- It is completely automated and thus removes any bias or subjectivity
- This system captures both gait geometry and gait dynamics (stance, swing, propulsion, etc)
- The sensitivity of the computer vision and bioinformatics allow PsychoGenics to capture symptoms of the disease model earlier and more accurately.

Gait analysis was measured when mice were 5, 6 and 7 weeks of age. Mice are placed in the NeuroCube® for a 5 min test. The most dominant of the features that define the disease phenotype (symptom descriptors) were identified and ranked. Complex bioinformatic algorithms were employed to calculate the discrimination probability between the WT and the Rett mice, and also to detect the test compound's ability to reverse the disease phenotype.

Feature Analysis

Ranking is an important part of the analyses because it weighs each feature change by its relevance: if there is a significant change in some irrelevant feature measured for a particular phenotype, the low rank of this feature will automatically reduce the effect of such change in our analyses.

Relative difference (%) between feature values in two different sets is calculated and plotted in the order corresponding to feature ranks together with their ranks varying from 0 to 100%.

Feature Analysis—List of Features Analyzed

1) Average Speed: measurement of average speed to travel the length of the NRC.
2) Body Position: using paw imaging parameters measures X and Y body coordinates, X and Y paw coordinates, and paw directional vectors as they pertain to movement of the subject's body.
3) Gait: measurements of geometry (e.g. Stride Length, Step Length, Base Width) and dynamics (e.g. Stride Duration, Step Duration, Swing Duration) of gait.
4) Imaging: measurements of the paw contact area, perimeter of contact zone, and paw diameter (horizontal/vertical).
5) Paw Position: the position of each paw print relative to the center of the body is registered. The overlay of all recorded relative positions of the four paws creates four clusters of points (one for each paw). For each paw, the coordinate of the cluster center, its size, the number of paw prints, and relative geometry of clusters positioning are measured.
6) Rhythmicity: correlation coefficients between gait signals of each paw and all others: RF-LF, RF-LH, RF-RH, LH-RH, LH-RF, LF-RH, LH-RH; (F—forelimb; H—hindlimb; R—right; L—left)

Feature Analysis: Quantitative Assessment of the Disease Phenotype

Figure 1:
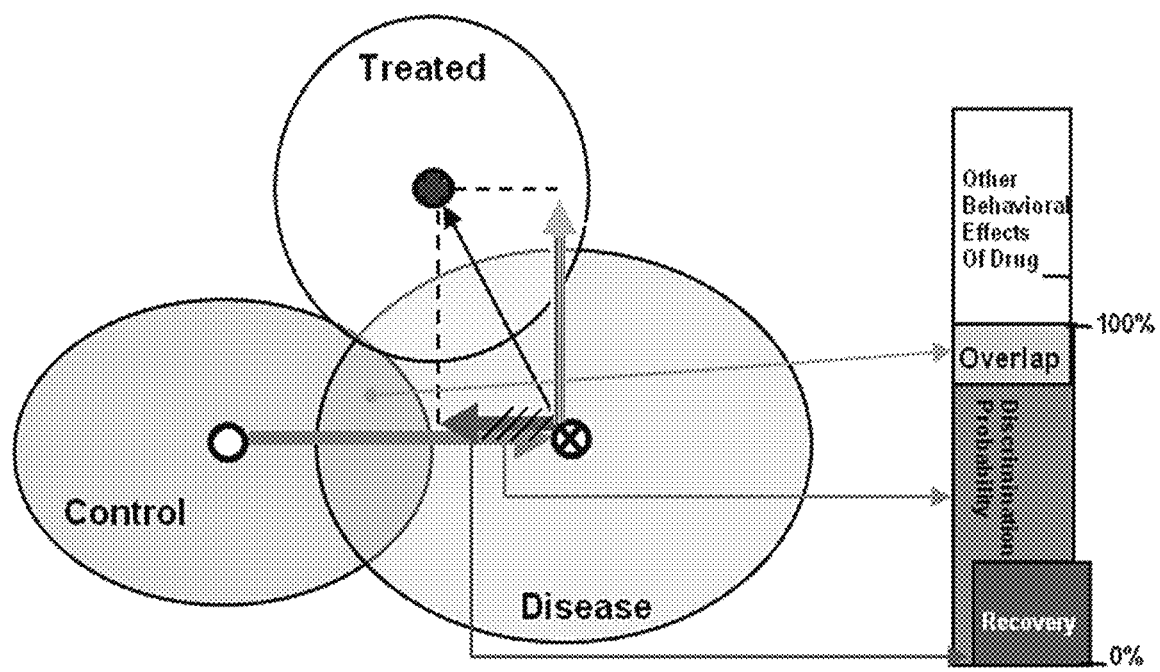
FIG. 1: Feature recovery as a measure of the therapeutic drug effect on Mecp2-KO Rett Syndrome model mice. The drug treatment effect can be represented as a combination of two components: one along the direction of the "recovery line" (the line connecting the centers of the control (WT) and disease (MECP2-KO) clouds, shown as a thick arrow to the left with diagonal lines on top), and the component orthogonal to ("pointing away" from) that direction shown as an arrow pointing up with parallel lines within. The relative length of the "recovery" arrow with respect to the control—disease distance can then be interpreted as the "recovery due to the drug", whereas the relative length of the "other effect" (orthogonal with parallel lines inside) arrow represents feature changes that move the disease mice+treatment group away from the control group. The summary of this analysis can be effectively represented as a bar graph (right pane in FIG. 1A) which is typically referred to as the recovery signature. Left: "the cloud graph": Visualization of the control—disease–(disease+treatment) groups relationship in the optimal discrimination feature space. The clouds are plotted in the two-dimensional space, the two coordinates being the highest ranked de-correlated features. Right: "the recovery signature" graph: The bar graph represents the summary of the recovery analysis. The overlap and discrimination probability sum up to 100%. The recovery ranges from 0 to the discrimination probability value. The lower the overlap, the better the quality of the disease model, and the higher the discrimination power between the WT and Rett mice groups. The "other behavioral effect" is in the same relative units (relative to the length of the distance between the WT and Rett mice groups).

In the feature space, the overlap between the "clouds" (Gaussian distributions approximating the groups of mice in the ranked de-correlated features space) serves as a quantitative measure of *separability* ("*distinguishability*") between the WT and Rett mice (see FIG. 1). For visualization purposes, we plot each cloud with its semi-axes equal to the one standard deviation along the corresponding dimensions.

Feature Analysis: Drug-Induced Recovery

In the "recovery-due-to-the-drug" experiments the data are typically presented by the three Classes: WT, Rett-KO, and Rett-KO+pridopidine treatment ('treated').

Therefore, it is instructive to consider (and plot) the third group, treated, in the same coordinate system that best discriminates the other groups (WT and Rett) as shown in FIG. 1A.

Treatment Groups

The following treatment groups were used in this study
1. WTmice-Vehicle
2. Rett-KO (B6.129P2-Mecp2tm2Bird/J) mice—Vehicle
3. Rett-KO (B6.129P2-Mecp2tm2Bird/J) mice—pridopidine (30 mg/kg BID)

Statistical Analysis

Data were analyzed by repeated measures analysis of variance (ANOVA) followed by posthoc comparisons where appropriate. An effect was considered significant if $p<0.05$. Data are represented as the mean and standard error to the mean (s.e.m).

Results:

NeuroCube®

1. Gait Features

Figure 11A:
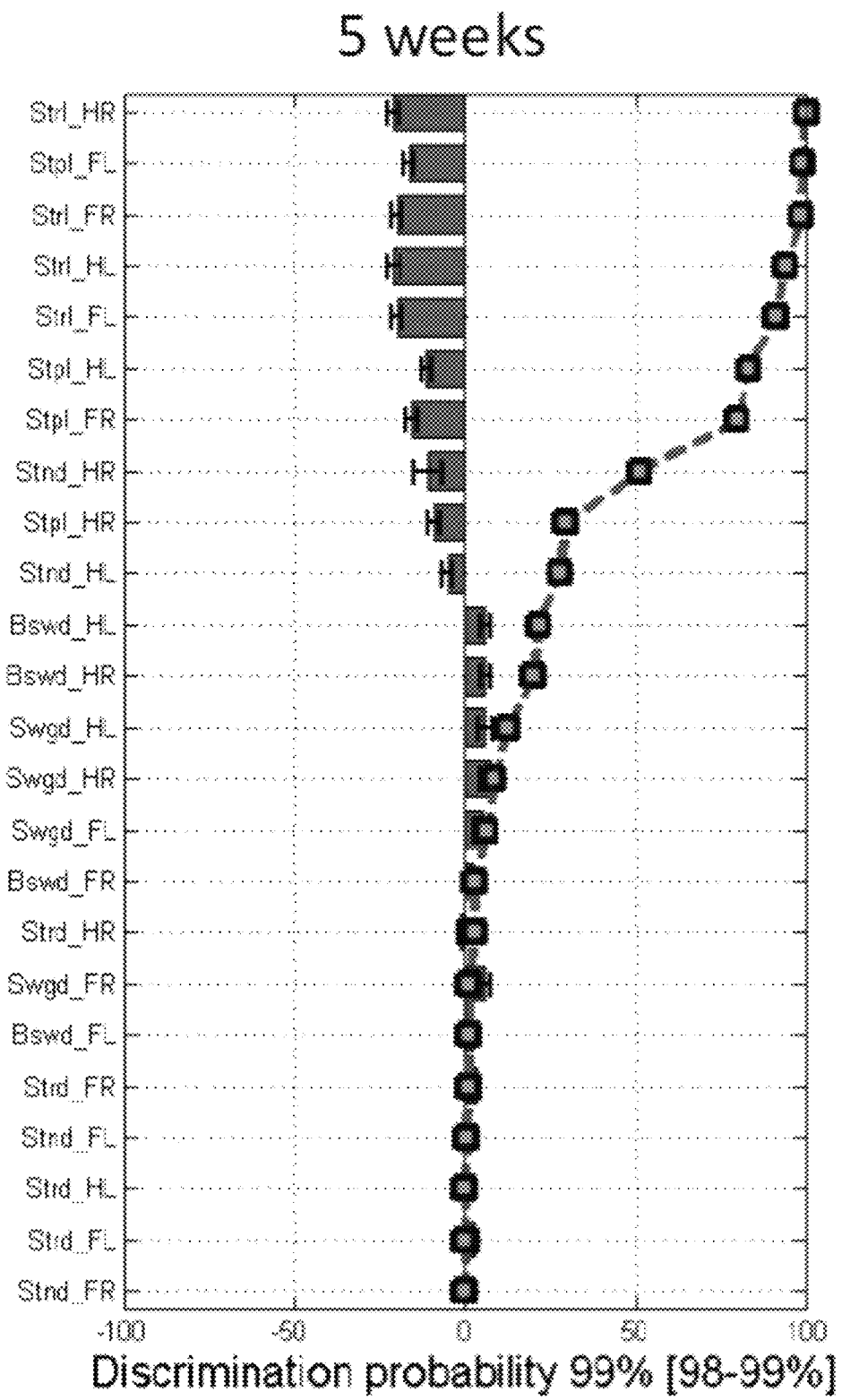
FIG. 11A-11C: In these experiments B6.129P2-Mecp2tm2Bird/J (Rett-KO) male mice were used. This figure displays discrimination plots of Rett-KO male mice compared to WT mice at 5(A), 6(B) and 7(C) weeks of age. Relative difference (%) between feature values in two different sets is calculated and plotted in the order corresponding to feature ranks together with their ranks varying from 0 to 100%.
Figure 11B:
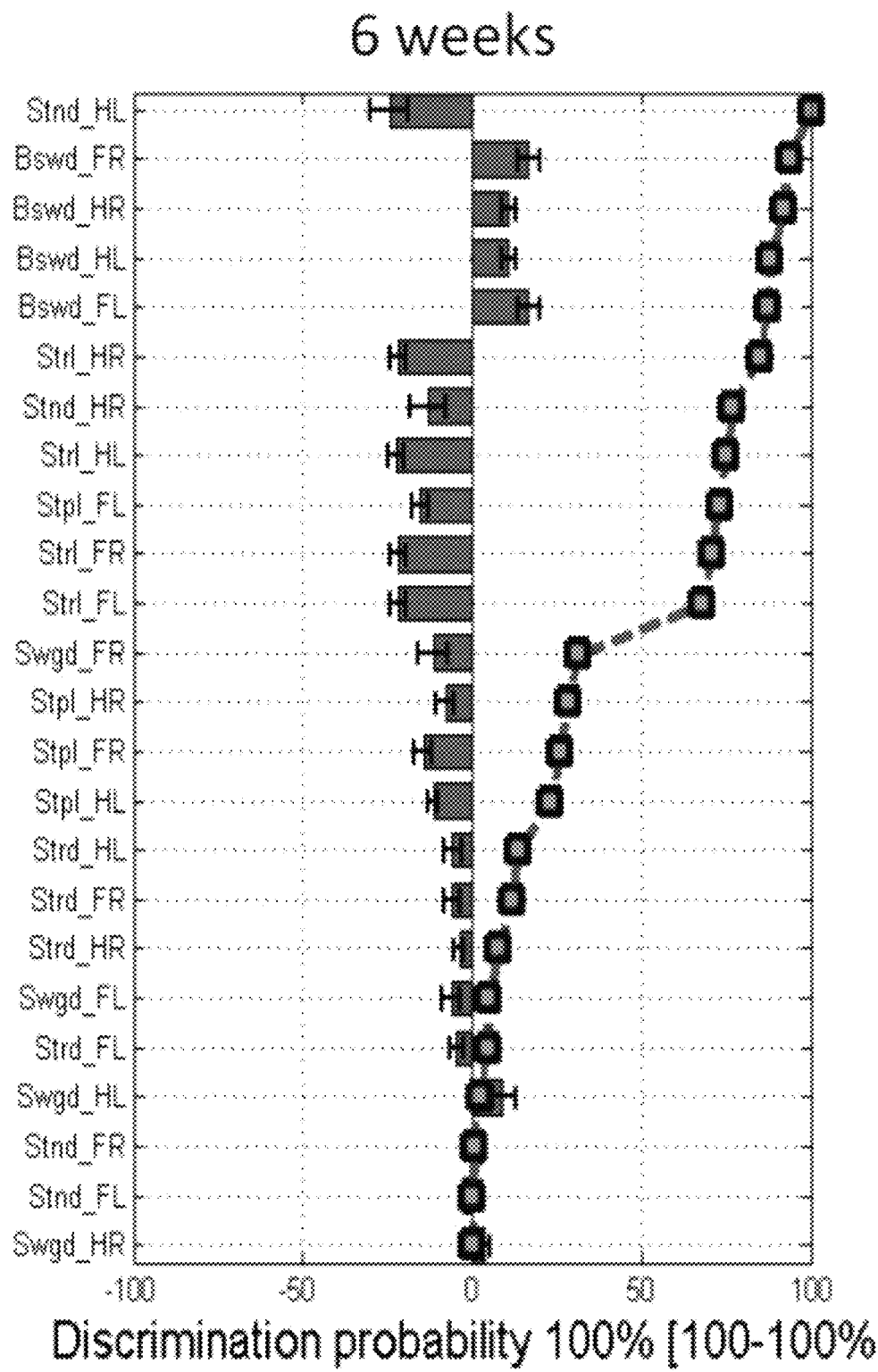
Figure 11C:
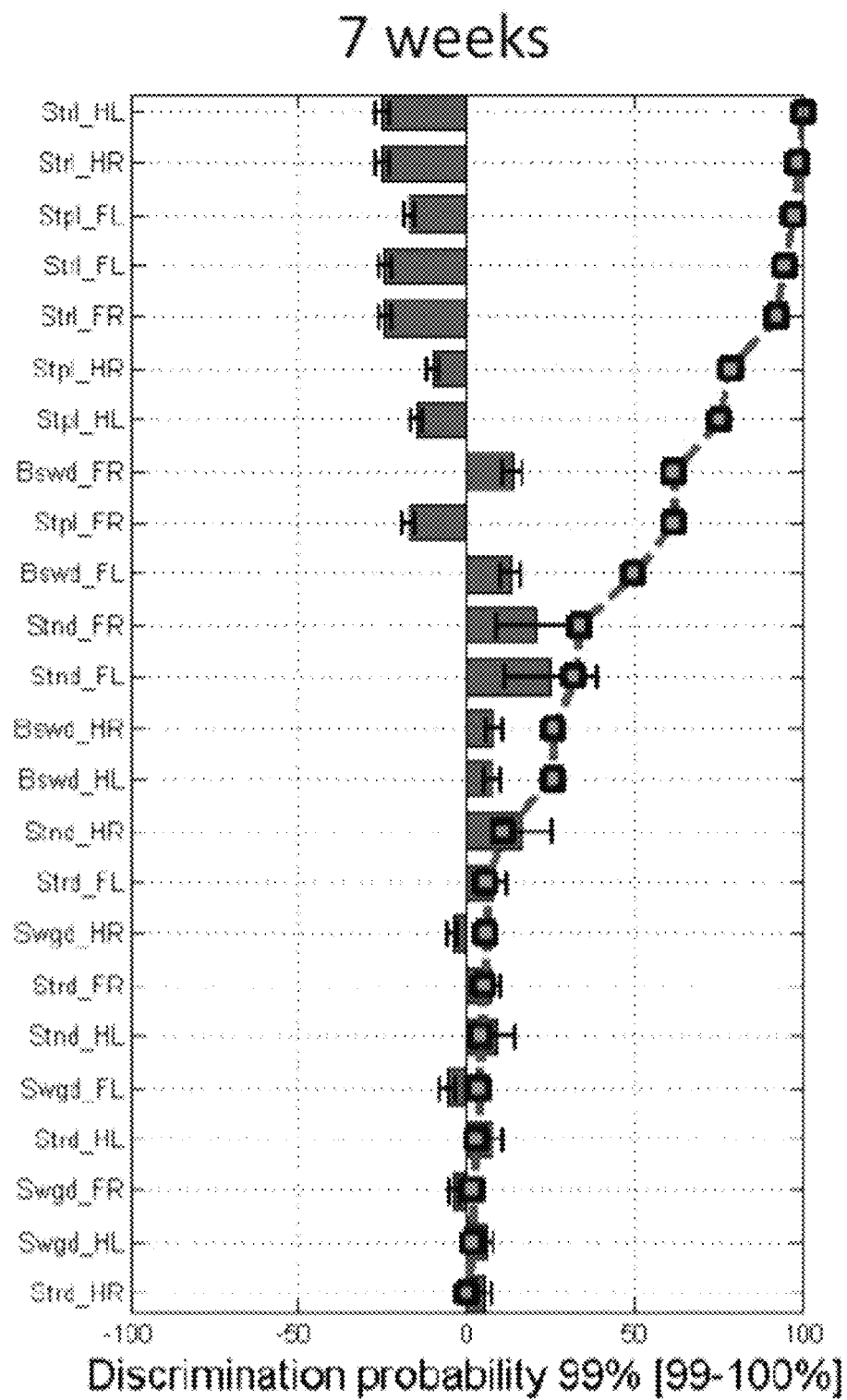

The discrimination plots of Rett-KO versus WT mice at 5, 6 and 7 weeks of age are shown in FIG. 11A-11C. Feature name is a combination of parameter name and the paw name. FR—for limb, right; FL—fore limb, left; HR—hind limb, right; HL—hind limb, left.

Analysis of gait features indicate that Rett-KO mice show gait deficits compared to WT mice at both 6 and 7 weeks of age with the discrimination probability of 100% and 99%, respectively. At 6 and 7 weeks of age, Rett-KO mice show deficits in the gait measurements of geometry, primarily stride length, base width and step length, compared to WT mice.

Figure 12:
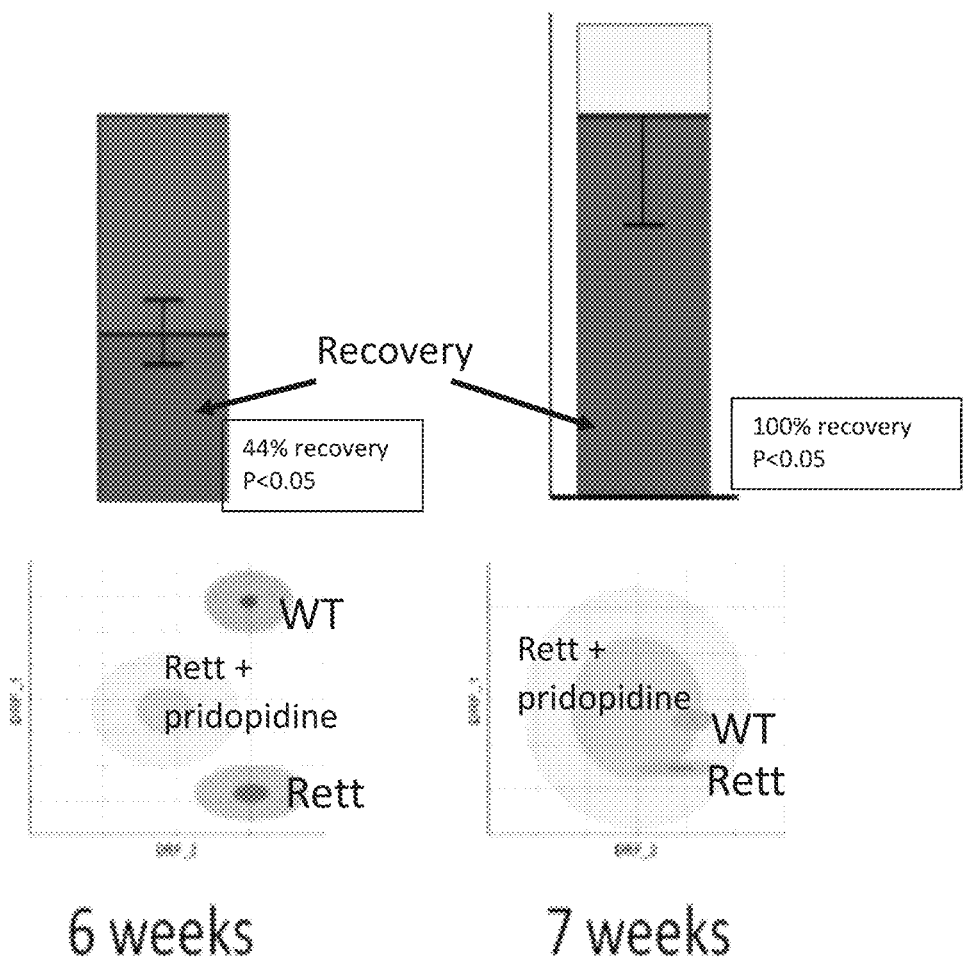
FIG. 12: Summary of recovery analysis from Rett syndrome effects in B6.129P2-Mecp2tm2Bird/J (Rett-KO) male mice. Top: bar graph showing the recovery effects of Pridopidine (30 mg/kg bid) in Rett-KO model mice. Middle: The cloud graph to visualize WT, Rett, and Rett+pridopidine relationship in the optimal discrimination feature space (WT, Rett, Rett+pridopidine). Pridopidine exhibits 44% (left, p<0.05) and 100% (right, p<0.05) recovery of gait deficits in Rett model mice at 6 and 7 weeks of age, respectively. One-way ANOVA.

The effects of Pridopidine (30 mg/kg BID) on gait deficits in Rett-KO mice were assessed when mice were 6 and 7 weeks of age. The summary of recovery is shown in FIG. 12. Pridopidine exhibits 44% and 100% recovery of gait deficits in Rett model mice at 6 and 7 weeks of age (both $p<0.05$, ANOVA).

Conclusions

Comparison of genotypes found that Rett-KO mice exhibit significant deficits in measurements of gait and compared to WT mice. The effects of chronic administration of Pridopidine (30 mg/kg/BID) in Rett-KO mice show significant gait recovery at 6 and 7 weeks.

Figure 13A:
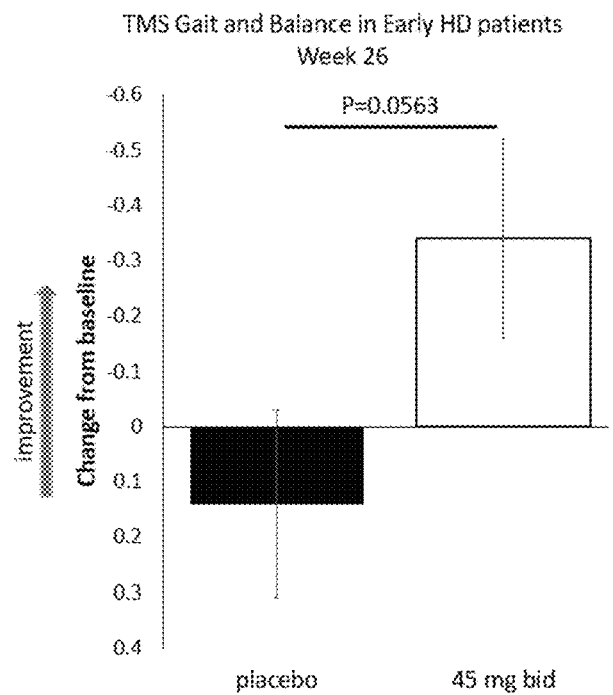
FIG. 13A-13B: Change from baseline in UHDRS TMS gait balances week 26 (A) and Week 52(B) in early HD (baseline TFC 7-13) patients in the PRIDE-HD study. Pridopidine efficacy was assessed throughout the 52-week period using Mixed Models Repeated Measures (MMRM) analyses of change from baseline in the Unified Huntington's Disease Rating Scale Total Motor Score gait and balance (UHDRS TMS; gait and balance).
Figure 13B:
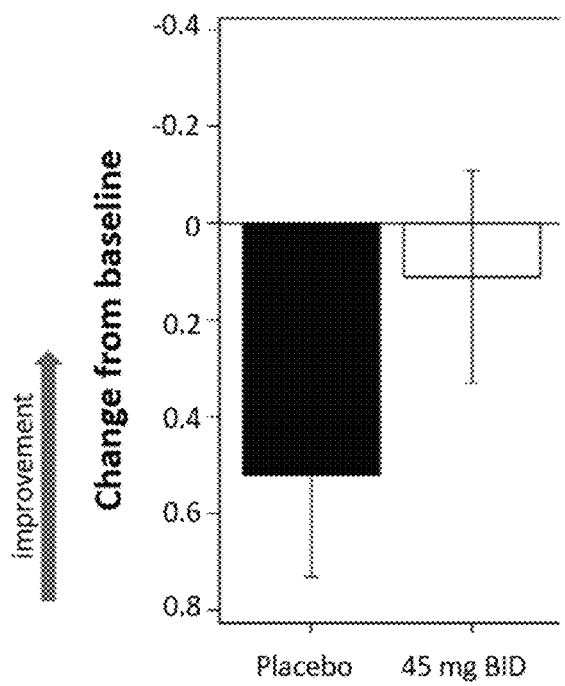

Example 4: Pridopidine 45 mg Bid Improves Gait and Balance in Early HD Patients at 52 Weeks Change from baseline in UHDRS TMS gait and balances scale at weeks 52 and 26 in early HD (baseline TFC 7-13). Table 1 (in the figure descriptions) and FIGS. 13A-13B show a trend towards improvement in UHDRS TMS gait and balances in early HD patients treated with pridopidine 45 mg bid compared to placebo at 52 weeks.

Early HD includes HD1 (TFC 11-13) and HD2 (TFC 7-10). FIG. 14A and table 2 (in the figure descriptions) display a significant effect of pridopidine 45 mg bid on change from baseline in gait and balance compared to placebo (p=0.0445). FIG. 14B shows a trend towards improvement at 26 weeks in pridopidine0treated HD1 patients. FIG. 15A-15B and Table 3 (in the figure descriptions) display a trend towards improvement of pridopidine 45 mg bid on change from baseline in gait and balance compared to placebo in HD2 patients at both 52 and 26 weeks.

Example 5: Assessment of Efficacy of Pridopidine in Treating Patients Afflicted with RTT Periodically administering pridopidine (e.g., daily or twice daily) intravenously or orally to a patient afflicted with Rett is effective to treat the patient.

Administering pridopidine effectively delays the onset of symptoms in the Rett patient.

Administering pridopidine effectively prevents or delays the worsening of, or improves at least one symptom in the Rett patient.

Administering pridopidine effectively prevents or delays the worsening of, or improves the mobility skill of the Rett patient. Administering pridopidine effectively prevents a partial or complete loss of acquired mobility skill of the Rett patient.

Administering pridopidine effectively prevents or delays the worsening of, or improves the gait of the Rett patient.

Administering pridopidine effectively prevents, delays or improves ataxia, apraxia, muscle weakness, spasticity, and/or rigidity in the Rett patient. Administering pridopidine effectively prevents, delays or improves impaired gait initiation in the Rett patient.

Administering pridopidine effectively prevents, delays or improves abnormal muscle tone, peripheral vasomotor disturbance, and/or scoliosis in the Rett patient.

Administering pridopidine effectively prevents or delays the worsening of, or improves purposeful hand skills in the Rett patient. Administering pridopidine effectively prevents, delays or improves abnormal hand movement, including but not limited to wringing, squeezing, clapping, washing, tapping, rubbing, and repeatedly bringing hands to mouth. Administering pridopidine effectively prevents a partial or complete loss of acquired purposeful hand skill of the Rett patient.

Administering pridopidine effectively prevents or delays the worsening of, or improves the communication skill of the Rett patient, including but not limited to speech and normal eye contact. Administering pridopidine effectively prevents a partial or complete loss of acquired communication skill of the Rett patient.

Administering pridopidine effectively prevents, delays or improves growth retardation, seizure, cardiac abnormality, breathing irregularity, impaired sleeping pattern, bruxism while awake, decreased response to pain, hypotrophic cold blue feet, increased irritability, decreased alertness, decreased attention span, inappropriate laughing, and/or inappropriate screaming.

REFERENCES

Amaral, M. D., et al. (2007) "TRPC channels as novel effectors of BDNF signaling: Potential implications for Rett syndrome". *Pharmacol Ther,* 113(2):394-409.

CSID:25948790, www.chemspider.com/Chemical-Structure.25948790.html (accessed 23:27, Jul. 15, 2016).

CSID:7971505, www.chemspider.com/Chemical-Structure.7971505.html (accessed 23:33, Jul. 15, 2016).

Geva, M. et al. Pridopidine activates neuroprotective pathways impaired in Huntington Disease. *Human Molecular Genetics,* 2016, 25(18):3975-3987

Guy J, Hendrich B, Holmes M, Martin J E, Bird A. (2001) A mouse MeCP2-null mutation causes neurological symptoms that mimic Rett syndrome. *Nat Genet.* 27(3): 322-326.

Isaias, I. U., et al. (2014). "Gait Initiation in Children with Rett Syndrome." *PLoS One,* 9(4): e92736.

Ponten H, Kullingsjö J, Lagerkvist S, Martin P, Pettersson F, Sonesson C, Waters S, Waters N. In vivo pharmacology of the dopaminergic stabilizer pridopidine. (2010) *Eur J Pharmacol.* 644(1-3):88-95.

Pozzo-Miller, L., Pati S., & Percy, A. K. (2015). "Rett Syndrome: Reaching for Clinical Trials." *Neurotherapeutics,* 12(3):631-40.

U.S. Publication No. 2013/0267552 A1 (Teva Pharmaceuticals International GMBH), published Oct. 10, 2013.

U.S. Publication No. 2014/0378508 (Teva Pharmaceuticals International GMBH), published Dec. 25, 2014.

U.S. Publication No. 2015/0202302 (Teva Pharmaceuticals International GMBH), published Jul. 23, 2015.

U.S. Pat. No. 7,923,459 (Teva Pharmaceuticals International GMBH), issued Apr. 12, 2011.

U.S. Pat. No. 6,903,120 (Teva Pharmaceuticals International GMBH), issued Jun. 7, 2015.

Weng, S. M. et al. (2011). "Rett Syndrome: From Bed to Bench." *Pediatrics and Neonatology,* 52:309-316.

What is claimed is:

1. A method for delaying the onset, preventing worsening, delaying worsening or improving at least one Rett symptom in the subject, wherein the Rett symptom is a partial or complete loss of acquired mobility skills; muscle weakness; abnormal eye movement; breathing irregularity; and/or cardiac abnormality; comprising administering to the subject an effective amount of pridopidine or pharmaceutically acceptable salt thereof so as to thereby delay the onset, prevent worsening, delay worsening or improve at least one Rett symptom.

2. The method of claim 1, wherein the pridopidine is pridopidine hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, the naphthalene-2-sulphonate, phthalate, salicylate, sorbate, stearate, succinate, tartrate or toluene-p-sulphonate salt.

3. The method of claim 1, wherein the pridopidine is administered orally, nasally, inhaled, by subcutaneous injection, or through an intravenous, intraperitoneal, intramuscular, intranasal, buccal, vaginal, rectal, intraocular, intrathecal, topical or intradermal route.

4. The method of claim 3, wherein the pridopidine is administered orally.

5. The method of claim 1, wherein the pridopidine is administered in the form of an aerosol, an inhalable powder, an injectable, a liquid, a gel, a solid, a capsule or a tablet.

6. The method of claim 1, wherein the pridopidine is administered periodically.

7. The method of claim 6, wherein the pridopidine is administered less often than once daily.

8. The method of claim 6, wherein the pridopidine is administered once daily or twice daily.

9. The method of claim 1, wherein the amount of pridopidine administered is 10 mg/day-315 mg/day.

10. The method of claim 1, wherein the amount of pridopidine administered is 45 mg/day-90 mg/day.

11. The method of claim 1, wherein the amount of pridopidine administered is 45 mg/day-180 mg/day.

12. The method of claim 9, wherein the amount of pridopidine administered is 20 mg/day, 22.5 mg/day, 45 mg/day, 67.5 mg/day, 90 mg/day, 100 mg/day, 112.5 mg/day, 125 mg/day, 135 mg/day, 150 mg/day, 180 mg/day, 200 mg/day, 225 mg/day, 250 mg/day, or 315 mg/day.

13. The method of claim 12, wherein the amount of pridopidine administered is 45 mg/day or 90 mg/day or 180 mg/day.

14. The method of claim 1, wherein the amount of pridopidine is administered in one dose or two doses per day.

15. The method of claim 14, wherein the amount of pridopidine administered in a dose is 10 mg, 22.5 mg, 45 mg, 67.5 mg, 90 mg, 100 mg, 112.5 mg, 125 mg, 135 mg, 150 mg, 180 mg, 200 mg, 250 mg, or 315 mg.

16. The method of claim 15, wherein the amount of pridopidine administered in a dose is 10 mg-45 mg.

17. The method of claim 16, wherein the amount of pridopidine is administered in two doses per day at an amount of 10 mg-45 mg per dose.

18. The method of f claim 1, wherein the pridopidine is first administered within 1 day, 1 week, 1 month, 3 months, 6 months, 9 months, 12 months, 18 months, 3 years, 5 years, 10 years, 15 years, 20 years, 25 years, or 30 years after birth of the subject.

19. The method of claim 6, wherein the periodic administration of pridopidine continues for at least 3 days, at least 30 days, at least 42 days, at least 8 weeks, at least 12 weeks, at least 24 weeks, at least 6 months, at least 1 year, at least 2 years, at least 5 years, at least 10 years, at least 15 years, at least 20 years, at least 25 years, or 30 years or more.

20. The method of claim 1, wherein the abnormal eye movement is prolonged staring, excessive blinking, crossed eyes, and/or closing one eye at a time.

21. The method of claim 1, wherein the pridopidine improves the symptom by at least 20%, at least 30%, at least 50%, at least 80%, or 100%.

22. The method of claim 1, wherein the pridopidine is effective to increase or maintain the brain-derived neurotrophic factor (BDNF) serum level in the subject and or to increase the brain-derived neurotrophic factor (BDNF) brain levels in the subject.

23. The method of claim 1, wherein the subject is a human patient.

24. The method of claim 1, wherein the subject has a mutation in at least one of the methyl CpG binding protein 2 (MeCP2) gene, the cyclin-dependent kinase-like 5 (CDKL5) gene or the Forkhead box protein G1 (FOXG1) gene.

25. A method of increasing BDNF serum level or brain-derived neurotrophic factor (BDNF) brain level in a subject afflicted with Rett comprising administering to the subject an effective amount of pridopidine so as to thereby increase BDNF serum level BDNF brain level in the subject.

* * * * *

SEQUENCE LISTING

<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: 5' Primer Sequence

<400> SEQUENCE: 1
ggcacaatgc aggaaagg                                                    18

<210> SEQ ID NO 2
<211> LENGTH: 21
<212> TYPE: DNA
<213> ORGANISM: Artificial Sequence
<220> FEATURE:
<223> OTHER INFORMATION: 3' Primer Sequence

<400> SEQUENCE: 2
tcagcaggca catagatagc c                                                21

<210> SEQ ID NO 3
<211> LENGTH: 19
<212> TYPE: DNA
<213> ORGANISM: Artificial Sequence
<220> FEATURE:
<223> OTHER INFORMATION: 5' Primer Sequence

<400> SEQUENCE: 3
ttgtggccaa gcaggtact                                                   19

<210> SEQ ID NO 4
<211> LENGTH: 20
<212> TYPE: DNA
<213> ORGANISM: Artificial Sequence
<220> FEATURE:
<223> OTHER INFORMATION: 3' Primer Sequence

<400> SEQUENCE: 4
gttgatgcct tcacagcgta                                                  20

<210> SEQ ID NO 5
<211> LENGTH: 21
<212> TYPE: DNA
<213> ORGANISM: Artificial Sequence
<220> FEATURE:
<223> OTHER INFORMATION: 5' Primer Sequence

<400> SEQUENCE: 5
caatgtgtcc gtcgtggatc t                                                21

<210> SEQ ID NO 6
<211> LENGTH: 22
<212> TYPE: DNA
<213> ORGANISM: Artificial Sequence
<220> FEATURE:
<223> OTHER INFORMATION: 3' Primer Sequence

<400> SEQUENCE: 6
gtcctcagtg tagcccaaga tg                                               22

<210> SEQ ID NO 7
<211> LENGTH: 20
<212> TYPE: DNA
<213> ORGANISM: Artificial Sequence
<220> FEATURE:
<223> OTHER INFORMATION: 5' Primer Sequence

<400> SEQUENCE: 7
agtctccagg acagcaaagc                                                  20

```
<210> SEQ ID NO 8
<211> LENGTH: 23
<212> TYPE: DNA
<213> ORGANISM: Artificial Sequence
<220> FEATURE:
<223> OTHER INFORMATION: 3' Primer Sequence

<400> SEQUENCE: 8
tgcaaccgaa gtatgaaata acc                                              23

<210> SEQ ID NO 9
<211> LENGTH: 22
<212> TYPE: DNA
<213> ORGANISM: Artificial Sequence
<220> FEATURE:
<223> OTHER INFORMATION: 5' Primer Sequence

<400> SEQUENCE: 9
gctgccttga tgtttacttt ga                                               22

<210> SEQ ID NO 10
<211> LENGTH: 23
<212> TYPE: DNA
<213> ORGANISM: Artificial Sequence
<220> FEATURE:
<223> OTHER INFORMATION: 3' Primer Sequence

<400> SEQUENCE: 10
aaggatggtc atcactcttc tca                                              23

<210> SEQ ID NO 11
<211> LENGTH: 19
<212> TYPE: DNA
<213> ORGANISM: Artificial Sequence
<220> FEATURE:
<223> OTHER INFORMATION: 5' Primer Sequence

<400> SEQUENCE: 11
ccgagagctt tgtgtggac                                                   19

<210> SEQ ID NO 12
<211> LENGTH: 21
<212> TYPE: DNA
<213> ORGANISM: Artificial Sequence
<220> FEATURE:
<223> OTHER INFORMATION: 3' Primer Sequence

<400> SEQUENCE: 12
tcatgcaacc gaagtatgaa a                                                21

<210> SEQ ID NO 13
<211> LENGTH: 20
<212> TYPE: DNA
<213> ORGANISM: Artificial Sequence
<220> FEATURE:
<223> OTHER INFORMATION: 5' Primer Sequence

<400> SEQUENCE: 13
gcctttggag cctcctctac                                                  20

<210> SEQ ID NO 14
<211> LENGTH: 19
<212> TYPE: DNA
<213> ORGANISM: Artificial Sequence
<220> FEATURE:
<223> OTHER INFORMATION: 3' Primer Sequence
```

```
<400> SEQUENCE: 14
gcggcatcca ggtaatttt                                              19
```